(12) United States Patent
Bryans et al.

(10) Patent No.: US 6,921,835 B2
(45) Date of Patent: Jul. 26, 2005

(54) CYCLIC AMINO ACIDS AND DERIVATIVES THEREOF USEFUL AS PHARMACEUTICAL AGENTS

(75) Inventors: Justin Stephen Bryans, Balsham (GB); David Christopher Horwell, Cambridge (GB); Andrew John Thorpe, Ann Arbor, MI (US); David Juergen Wustrow, Ann Arbor, MI (US); Po-Wai Yuen, Ann Arbor, MI (US)

(73) Assignee: Warner Lambert Company, Morris Plains, NJ (US)

( * ) Notice: Subject to any disclaimer, the term of this patent is extended or adjusted under 35 U.S.C. 154(b) by 0 days.

(21) Appl. No.: 10/448,834

(22) Filed: May 30, 2003

(65) Prior Publication Data

US 2003/0220397 A1 Nov. 27, 2003

Related U.S. Application Data

(63) Continuation of application No. 09/485,382, filed as application No. PCT/US98/19876 on Sep. 23, 1998, now Pat. No. 6,635,673.
(60) Provisional application No. 60/063,644, filed on Oct. 27, 1997, and provisional application No. 60/097,685, filed on Aug. 24, 1998.

(51) Int. Cl.$^7$ .......................... C07C 61/06; C07C 61/04
(52) U.S. Cl. ...................................... 562/504; 562/505
(58) Field of Search ................................ 562/504, 505, 562/503; 560/121, 122, 123

(56) References Cited

U.S. PATENT DOCUMENTS

| 4,024,175 A | 5/1977 | Satzinger et al. |
| 4,087,544 A | 5/1978 | Satzinger et al. ............ 424/305 |
| 4,152,326 A | 5/1979 | Hartenstein et al. .......... 546/16 |
| 5,025,035 A | 6/1991 | Wallace ...................... 514/530 |
| 5,068,413 A | 11/1991 | Steiner et al. ............... 562/507 |
| 5,084,479 A | 1/1992 | Woodruff ..................... 514/530 |
| 5,132,451 A | 7/1992 | Jennings et al. ............ 562/507 |
| 5,210,385 A | 5/1993 | Saito et al. .................. 568/385 |
| 5,319,135 A | 6/1994 | Jennings et al. ............ 562/507 |
| 5,362,883 A | 11/1994 | Jennings et al. ............ 548/408 |
| 5,510,381 A | 4/1996 | Pande ......................... 514/561 |
| 5,631,291 A | 5/1997 | Mittendorf et al. ......... 514/561 |

FOREIGN PATENT DOCUMENTS

| CA | 1085420 | 9/1980 |
| EP | 0458751 | 11/1991 |
| WO | 9307111 | 4/1993 |
| WO | 9519337 | 7/1995 |
| WO | 9603122 | 2/1996 |
| WO | WO 97/33858 | 9/1997 |

OTHER PUBLICATIONS

Gee et al., "The Novel Anticonvulsant Drug, Gabapentin (Neurontin), Binds to the alpha2delta Subunit of a Calcium Channel", The Journal of Biological Chemistry, vol. 271, No. 10, 1996, pp. 5768–5776.

Su et al., "Transport of Gabapentin, a γ–Amino Acid Drug, by System L alpha–Amino Acid Transporters: A Comparative Study in Astrocytes, Synaptosomes, and CHO Cells", Journal of Neurochemistry, vol. 64, 1995, pp. 2125–2131.

James and Fischer, "Transport of Neutral Amino Acids at the Blood–Brain Barrier", Pharmacology, vol. 22, 1981, pp. 1–7.

Suman–Chauhan et al., "Characterisation of [$^3$H]gabapentin binding to a novel site in rat brain: homogenate binding studies", Eur. J. Pharmacol., Mol. Pharmacol. Sect., vol. 244, No. 3, 1993, pp 293–301.

Mason et al., "Influence of Bond Angle Distortion and α–æ–Delocalization on the Stability and Chemistry of Allylic Cations", J. Am. Chem. Soc., vol. 95, No. 6, 1973, pp 1849–1859.

Müller and Pautex, "122. Rh(II)–Catalyzed Isomerizations of Cyclopropenes", Helv. Chim. Acta. vol. 73, No. 5, 1990, pp 1233–1241.

Piva and Comesse, "Tandem Michaël–Wittig Horner Reaction One–Pot Synthesis of Δ–Substituted αβ Unsaturated Esters", Tetrahedron Lett., vol. 38, No. 41, 1997, pp 7191–7194.

Müller and Gränicher, "33. Structural Effects on the Rh$^{13}$ – Catalyzed Rearrangement of Cyclopropenes", Helv. Chim. Acta, vol. 76, No. 1, 1993, pp 521–534.

Bunce and Drumright, "Michael Reaction of Nitromethane with ββ–Disubstituted Acrylate Esters", Org. Prep. Proced. Int., vol. 19, No. 6, 1987, pp 471–475.

Sircar, "Die Herstellung von substituierten Butyrolactamen", Chem. Zentralbl., vol. 100, No. 1, 1929, p 741.

Urabe et al., "Intramolecular Cyclization of 2,7– or 2,8–Bis–unsaturated Esters Mediated by (β$^2$–Propene)Ti(O–i–Pr)$_2$. Facile Construction of Mono– and Bicyclic Skeletons with Stereoselective Introduction of a Side Chain. A Synthesis of d–Sabinene", J. Am. Chem. Soc., vol. 119, No. 42, 1997, pp 10014–10027.

(Continued)

Primary Examiner—Paul A. Zucker
(74) Attorney, Agent, or Firm—Mehdi Ganjeizadeh; Charles Ashbrook

(57) ABSTRACT

The invention is a novel series of cyclic amino acids which are useful in the treatment of epilepsy, faintness attacks, neurodegenerative disorders, depression, anxiety, panic, pain, neuropathological disorders, gastrointestinal disorders such as irritable bowel syndrome (IBS), and inflammation, especially arthritis. A pharmaceutical composition containing a compound of the invention as well as methods of preparing the compounds and novel intermediates useful in the preparation of the final compounds are included.

5 Claims, No Drawings

OTHER PUBLICATIONS

Suzuki et al., "A Novel tandem Cyclization of 2,7– or 2,8–Bis–Unsaturated Esters Mediated by ç²–Propene)TiX₂ (X=Cl or O–i–Pr). A Facile Construction of Bicyclo[3.3.0] octane, –[4.3.0]nonane, and—[3.1.0]hexane Skeletons", *J. Am. Chem. Soc.*, vol. 118, No. 36, 1996, pp 8729–8730.

Hiouni and Duhamel, "2,2–Di(ethoxy)vinyllithium: Reactions with Carbonyl Compounds", *Tetrahedron Lett.*, vol. 37, No. 31, 1996, pp 5507–5510.

de Meijere et al., "Unprecendented Addition of Dialkoxycarbenes to Tetrasubstituted Alkenes: Bicyclopropylidene and 2–Chlorocyclopropylideneacetate", *Liebigs Ann.*, vol. 4, 1996, pp 601–612.

Müller and Gränicher, "11. Selectivity in Rhodium(II)–Catalyzed Rearrangements of Cycloprop–2–ene–1–carboxylates", *Helv. Chim. Acta*, vol. 78, No. 1, 1995, pp 129–144.

Gil and Fiaud, "Selectivities in the palladium–catalyzed synthesis of dimethyl [2–(3–substituted cyclobutylidene) ethyl]malonate", *Bull. Soc. Chim. Fr.*, vol. 131, No. 5, 1994, pp 584–589.

Narasaka et al., "Kinetic Resolution of a–Substituted Ketones by Wittig Reaction using a Chiral Tricyclic Phosphonate", *J. Chem. Soc., Chem. Commun.*, vol. 2, 1993, pp 102–104.

Fiaud et al., "Kinetic Resolution of 3–tButyl and 3–Phenyl Cyclobutylidenethanols through Lipase–catalyzed Acylation with Succinic Anhydride", *Tetrahedron Lett.*, vol. 33, No. 46, 1992, pp 6967–6970.

Sugahara et al., "Total Synthesis of (+)–Polyzonimine", *J. Chem. Soc., Chem. Commun.*, vol. 4, 1984, pp 214–215.

Ibuka and Minakata, "a– and Γ–Substituted reactions of cyclic Γ–acetoxy–a,β–unsaturated esters with a novel reagent BuCu–AlCl₃", *Synth. Commun*, vol. 10, No. 2, 1980, pp 119–125.

Gajewski and Burka, "Alkyl Shifts in Thermolysea. VII. Stereochemistry and Kinetics of the Carbethoxyspiropentane to Carbethoxymethylenecyclobutane Rearrangement. Evidence for Concertion and an Intermediate", *J. Am. Chem. Soc.*, vol. 94, No. 25, 1972, pp 8865–8875.

Gajewski and Burka, "Alkyl Shifts in Thermolyses. IV. Carbethoxyspiropentane–Carbethoxymethylenecyclobutane Isomerization. Evidence for Orbital Symmetry Control and an Intermediate", *J. Am. Chem. Soc.*, vol. 94, No. 7, 1972, pp 2554–2556.

Erickson, "Reaction of 1–Bromomethylene–2,2–dimethylcyclobutane with Potassium *tert*–Butoxide", *J. Org. Chem.*, vol. 36, No. 8, 1971, pp 1031–1036.

Jorgenson and Patumtevapibal, "Ring size and conformational effects of photodeconjugation of cycloalkylidene esters", *Tetrahedron Lett.*, vol. 7, 1970, pp 489–492.

Kon et al., "361. The Chemistry of the Three–carbon System. Part XXIX. Tautomerism of Unsaturated Esters.", *J. Chem. Soc.*, 1932, pp 2454–2459.

Winternitz et al., "No. 31. Syntheses de substances polycycliques (VI. memoire). Acides phenylcyclopentylacetiques", *Bull. Soc. Chim. Fr.*, 1953, pp 190–195.

Derwent abstract, DT 2543–821, Godecke AG.

Derwent abstract, DT 2626–467, Godecke AG.

Derwent abstract, EP 414 263 A, Godecke AG.

US 6,921,835 B2

CYCLIC AMINO ACIDS AND DERIVATIVES THEREOF USEFUL AS PHARMACEUTICAL AGENTS

CROSS-REFERENCE TO RELATED APPLICATIONS

This is a continuation of Ser. No. 09/485,382 filed Feb. 8, 2000, now U.S. Pat. No. 6,635,673, which is a 371 filing of PCT/US98/19876 filed Sep. 23, 1998, which claims priority to U.S. Provisional Ser. No. 60/063,644 filed Oct. 27, 1997, and U.S. Provisional Ser. No. 60/097,685 filed Aug. 24, 1998.

BACKGROUND OF THE INVENTION

Compounds of formula

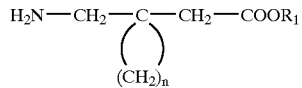

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The compounds of the invention are those of formulas 1 and 1A

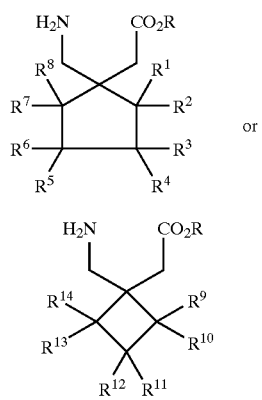

wherein R to $R^{14}$ are as defined below.

The compounds of the invention and their pharmaceutically acceptable salts and the prodrugs of the compounds, are useful in the treatment of epilepsy, faintness attacks, hypokinesia, cranial disorders, neurodegenerative disorders, depression, anxiety, panic, pain, neuropathological disorders, gastrointestinal disorders such as irritable bowel syndrome (IBS), and inflammation, especially arthritis.

The invention is also a pharmaceutical composition of a compound of formulas 1 and 1A.

DETAILED DESCRIPTION OF THE INVENTION

The compounds of the instant invention and their pharmaceutically acceptable salts are as defined by formulas 1 and 1A

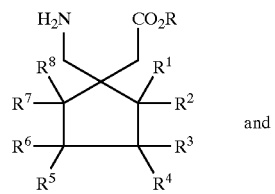

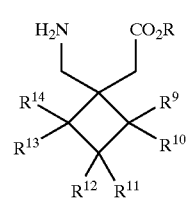

or a pharmaceutically acceptable salt thereof wherein:
R is hydrogen or a lower alkyl;
$R^1$ to $R^{14}$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, —$CO_2H$, —$CO_2R^{15}$, —$CH_2CO_2H$, —$CH_2CO_2R^{15}$, —$OR^{15}$ wherein $R^{15}$ is a straight or branched alkyl of from 1 to 6 carbons, phenyl, or benzyl, and $R^1$ to $R^8$ are not simultaneously hydrogen.

Preferred compounds of the invention are those of Formula I wherein $R^1$ to $R^{14}$ are selected from hydrogen, methyl, ethyl, propyl, isopropyl, butyl straight or branched, phenyl, or benzyl.

More preferred compounds are those of Formula I wherein $R^1$ to $R^{14}$ are selected from hydrogen, methyl, ethyl, or benzyl.

The most preferred compounds are selected from:
(1α,3α,4α)-(1-Aminomethyl-3,4-dimethyl-cyclopentyl)-acetic acid;
(1α,3α,4α)-(1-Aminomethyl-3,4-diethyl-cyclopentyl)-acetic acid;
(1α,3α,4α)-(1-Aminomethyl-3,4-diisopropyl-cyclopentyl)-acetic acid;
[1S-(1α,3α,4α)]-(1-Aminomethyl-3-ethyl-4-methyl-cyclopentyl)-acetic acid;
[1R-(1α,3α,4α)]-(1-Aminomethyl-3-ethyl-4-methyl-cyclopentyl)-acetic acid;
[1S-(1α,3α,4α)]-(1-Aminomethyl-3-isopropyl-4-methyl-cyclopentyl)-acetic acid;
[1R-(1α,3α,4α)]-(1-Aminomethyl-3-isopropyl-4-methyl-cyclopentyl)-acetic acid;
[1S-(1α,3α,4α)]-(1-Aminomethyl-3-ethyl-4-isopropyl-cyclopentyl)-acetic acid;
[1R-(1α,3α,4α)]-(1-Aminomethyl-3-ethyl-4-isopropyl-cyclopentyl)-acetic acid;
[1S-(1α,3α,4α)]-(1-Aminomethyl-3-tert-butyl-4-methyl-cyclopentyl)-acetic acid;
[1R-(1α,3α,4α)]-(1-Aminomethyl-3-tert-butyl-4-methyl-cyclopentyl)-acetic acid;
[1S-(1α,3α,4α)]-(1-Aminomethyl-3-tert-butyl-4-ethyl-cyclopentyl)-acetic acid;
[1R-(1α,3α,4α)]-(1-Aminomethyl-3-tert-butyl-4-ethyl-cyclopentyl)-acetic acid;

[1S-(1α,3α,4α)]-(1-Aminomethyl-3-tert-butyl-4-isopropyl-cyclopentyl)-acetic acid;
[1R-(1α,3α,4α)]-(1-Aminomethyl-3-tert-butyl-4-isopropyl-cyclopentyl)-acetic acid;
(1α,3α,4α)-(1-Aminomethyl-3,4-di-tert-butyl-cyclopentyl)-acetic acid;
[1S-(1α,3α,4α)]-(1-Aminomethyl-3-methyl-4-phenyl-cyclopentyl)-acetic acid;
[1R-(1α,3α,4α)]-(1-Aminomethyl-3-methyl-4-phenyl-cyclopentyl)-acetic acid;
[1S-(1α,3α,4α)]-(1-Aminomethyl-3-benzyl-4-methyl-cyclopentyl)-acetic acid;
[1R-(1α,3α,4α)]-(1-Aminomethyl-3-benzyl-4-methyl-cyclopentyl)-acetic acid;
(1S-cis)-(1-Aminomethyl-3-methyl-cyclopentyl)-acetic acid;
(1S-cis)-(1-Aminomethyl-3-ethyl-cyclopentyl)-acetic acid;
(1S-cis)-(1-Aminomethyl-3-isopropyl-cyclopentyl)-acetic acid;
(1S-cis)-(1-Aminomethyl-3-tert-butyl-cyclopentyl)-acetic acid;
(1S-cis)-(1-Aminomethyl-3-phenyl-cyclopentyl)-acetic acid;
(1S-cis)-(1-Aminomethyl-3-benzyl-cyclopentyl)-acetic acid;
(1R-cis)-(1-Aminomethyl-3-methyl-cyclopentyl)-acetic acid;
(1R-cis)-(1-Aminomethyl-3-ethyl-cyclopentyl)-acetic acid;
(1R-cis)-(1-Aminomethyl-3-isopropyl-cyclopentyl)-acetic acid;
(1R-cis)-(1-Aminomethyl-3-tert-butyl-cyclopentyl)-acetic acid;
(1R-cis)-(1-Aminomethyl-3-phenyl-cyclopentyl)-acetic acid;
(1R-cis)-(1-Aminomethyl-3-benzyl-cyclopentyl)-acetic acid;
(S)-(1-Aminomethyl-3,3-dimethyl-cyclopentyl)-acetic acid;
(S)-(1-Aminomethyl-3,3-diethyl-cyclopentyl)-acetic acid;
(1-Aminomethyl-3,3,4,4-tetramethyl-cyclopentyl)-acetic acid;
(1-Aminomethyl-3,3,4,4-tetraethyl-cyclopentyl)-acetic acid;
(1α,3β,4β)-(1-Aminomethyl-3,4-dimethyl-cyclopentyl)-acetic acid;
(1α,3β,4β)-(1-Aminomethyl-3,4-diethyl-cyclopentyl)-acetic acid;
(1α,3β,4β)-(1-Aminomethyl-3,4-diisopropyl-cyclopentyl)-acetic acid;
[1R-(1α,3β,4β)]-(1-Aminomethyl-3-ethyl-4-methyl-cyclopentyl)-acetic acid;
[1S-(1α,3β,4β)]-(1-Aminomethyl-3-ethyl-4-methyl-cyclopentyl)-acetic acid;
[1R-(1α,3β,4β)]-(1-Aminomethyl-3-isopropyl-4-methyl-cyclopentyl)-acetic acid;
[1S-(1α,3β,4β)]-(1-Aminomethyl-3-isopropyl-4-methyl-cyclopentyl)-acetic acid;
[1R-(1α,3β,4β)]-(1-Aminomethyl-3-ethyl-4-isopropyl-cyclopentyl)-acetic acid;
[1S-(1α,3β,4β)]-(1-Aminomethyl-3-ethyl-4-isopropyl-cyclopentyl)-acetic acid;
[1R-(1α,3β,4β)]-(1-Aminomethyl-3-tert-butyl-4-methyl-cyclopentyl)-acetic acid;
[1S-(1α,3β,4β)]-(1-Aminomethyl-3-tert-butyl-4-methyl-cyclopentyl)-acetic acid;
[1R-(1α,3β,4β)]-(1-Aminomethyl-3-tert-butyl-4-ethyl-cyclopentyl)-acetic acid;
[1S-(1α,3β,4β)]-(1-Aminomethyl-3-tert-butyl-4-ethyl-cyclopentyl)-acetic acid;
[1R-(1α,3β,4β)]-(1-Aminomethyl-3-tert-butyl-4-isopropyl-cyclopentyl)-acetic acid;
[1S-(1α,3β,4β)]-(1-Aminomethyl-3-tert-butyl-4-isopropyl-cyclopentyl)-acetic acid;
(1α,3β,4β)-(1-Aminomethyl-3,4-di-tert-butyl-cyclopentyl)-acetic acid;
[1R-(1α,3β,4β)]-(1-Aminomethyl-3-methyl-4-phenyl-cyclopentyl)-acetic acid;
[1S-(1α,3β,4β)]-(1-Aminomethyl-3-methyl-4-phenyl-cyclopentyl)-acetic acid;
[1R-(1α,3β,4β)]-(1-Aminomethyl-3-benzyl-4-methyl-cyclopentyl)-acetic acid;
[1S-(1α,3β,4β)]-(1-Aminomethyl-3-benzyl-4-methyl-cyclopentyl)-acetic acid;
(1R-trans)-(1-Aminomethyl-3-methyl-cyclopentyl)-acetic acid;
(1R-trans)-(1-Aminomethyl-3-ethyl-cyclopentyl)-acetic acid;
(1R-trans)-(1-Aminomethyl-3-isopropyl-cyclopentyl)-acetic acid;
(1R-trans)-(1-Aminomethyl-3-tert-butyl-cyclopentyl)-acetic acid;
(1R-trans)-(1-Aminomethyl-3-phenyl-cyclopentyl)-acetic acid;
(1R-trans)-(1-Aminomethyl-3-benzyl-cyclopentyl)-acetic acid;
(1S-trans)-(1-Aminomethyl-3-methyl-cyclopentyl)-acetic acid;
(1S-trans)-(1-Aminomethyl-3-ethyl-cyclopentyl)-acetic acid;
(1S-trans)-(1-Aminomethyl-3-isopropyl-cyclopentyl)-acetic acid;
(1S-trans)-(1-Aminomethyl-3-tert-butyl-cyclopentyl)-acetic acid;
(1S-trans)-(1-Aminomethyl-3-phenyl-cyclopentyl)-acetic acid;
(1S-trans)-(1-Aminomethyl-3-benzyl-cyclopentyl)-acetic acid;
(R)-(1-Aminomethyl-3,3-dimethyl-cyclopentyl)-acetic acid;
(R)-(1-Aminomethyl-3,3-diethyl-cyclopentyl)-acetic acid;
cis-(1-Aminomethyl-3-methyl-cyclobutyl)-acetic acid;
cis-(1-Aminomethyl-3-ethyl-cyclobutyl)-acetic acid;
cis-(1-Aminomethyl-3-isopropyl-cyclobutyl)-acetic acid;
cis-(1-Aminomethyl-3-tert-butyl-cyclobutyl)-acetic acid;
cis-(1-Aminomethyl-3-phenyl-cyclobutyl)-acetic acid;
cis-(1-Aminomethyl-3-benzyl-cyclobutyl)-acetic acid;
trans-(1-Aminomethyl-3-methyl-cyclobutyl)-acetic acid;
trans-(1-Aminomethyl-3-ethyl-cyclobutyl)-acetic acid;
trans-(1-Aminomethyl-3-isopropyl-cyclobutyl)-acetic acid;
trans-(1-Aminomethyl-3-tert-butyl-cyclobutyl)-acetic acid;
trans-(1-Aminomethyl-3-phenyl-cyclobutyl)-acetic acid;
trans-(1-Aminomethyl-3-benzyl-cyclobutyl)-acetic acid;
cis-(1-Aminomethyl-3-ethyl-3-methyl-cyclobutyl)-acetic acid;
cis-(1-Aminomethyl-3-isopropyl-3-methyl-cyclobutyl)-acetic acid;
cis-(1-Aminomethyl-3-tert-butyl-3-methyl-cyclobutyl)-acetic acid;
cis-(1-Aminomethyl-3-methyl-3-phenyl-cyclobutyl)-acetic acid;
cis-(1-Aminomethyl-3-benzyl-3-methyl-cyclobutyl)-acetic acid;
trans-(1-Aminomethyl-3-ethyl-3-methyl-cyclobutyl)-acetic acid;
trans-(1-Aminomethyl-3-isopropyl-3-methyl-cyclobutyl)-acetic acid;
trans-(1-Aminomethyl-3-tert-butyl-3-methyl-cyclobutyl)-acetic acid;

trans-(1-Aminomethyl-3-methyl-3-phenyl-cyclobutyl)-acetic acid;
trans-(1-Aminomethyl-3-benzyl-3-methyl-cyclobutyl)-acetic acid;
cis-(1-Aminomethyl-3-ethyl-3-isopropyl-cyclobutyl)-acetic acid;
cis-(1-Aminomethyl-3-tert-butyl-3-ethyl-cyclobutyl)-acetic acid;
cis-(1-Aminomethyl-3-ethyl-3-phenyl-cyclobutyl)-acetic acid;
cis-(1-Aminomethyl-3-benzyl-3-ethyl-cyclobutyl)-acetic acid;
trans-(1-Aminomethyl-3-ethyl-3-isopropyl-cyclobutyl)-acetic acid;
trans-(1-Aminomethyl-3-tert-butyl-3-ethyl-cyclobutyl)-acetic acid;
trans-(1-Aminomethyl-3-ethyl-3-phenyl-cyclobutyl)-acetic acid;
trans-(1-Aminomethyl-3-benzyl-3-ethyl-cyclobutyl)-acetic acid;
cis-(1-Aminomethyl-3-tert-butyl-3-isopropyl-cyclobutyl)-acetic acid;
cis-(1-Aminomethyl-3-isopropyl-3-phenyl-cyclobutyl)-acetic acid;
trans-(1-Aminomethyl-3-benzyl-3-isopropyl-cyclobutyl)-acetic acid;
cis-(1-Aminomethyl-3-tert-butyl-3-phenyl-cyclobutyl)-acetic acid;
trans-(1-Aminomethyl-3-benzyl-3-tert-butyl-cyclobutyl)-acetic acid;
trans-(1-Aminomethyl-3-tert-butyl-3-isopropyl-cyclobutyl)-acetic acid;
trans-(1-Aminomethyl-3-isopropyl-3-phenyl-cyclobutyl)-acetic acid;
cis-(1-Aminomethyl-3-benzyl-3-isopropyl-cyclobutyl)-acetic acid;
trans-(1-Aminomethyl-3-tert-butyl-3-phenyl-cyclobutyl)-acetic acid;
cis-(1-Aminomethyl-3-benzyl-3-tert-butyl-cyclobutyl)-acetic acid;
(1-Aminomethyl-3,3-dimethyl-cyclobutyl)-acetic acid;
(1-Aminomethyl-3,3-diethyl-cyclobutyl)-acetic acid;
(1-Aminomethyl-3,3-diisopropyl-cyclobutyl)-acetic acid;
(1-Aminomethyl-3,3-di-tert-butyl-cyclobutyl)-acetic acid;
(1-Aminomethyl-3,3-diphenyl-cyclobutyl)-acetic acid;
(1-Aminomethyl-3,3-dibenzyl-cyclobutyl)-acetic acid;
(1-Aminomethyl-2,2,4,4-tetramethyl-cyclobutyl)-acetic acid;
(1-Aminomethyl-2,2,3,3,4,4-hexamethyl-cyclobutyl)-acetic acid;
(R)-(1-Aminomethyl-2,2-dimethyl-cyclobutyl)-acetic acid;
(S)-(1-Aminomethyl-2,2-dimethyl-cyclobutyl)-acetic acid;
(1R-cis)-(1-Aminomethyl-2-methyl-cyclobutyl)-acetic acid;
[1R-(1α,2α,3α)]-(1-Aminomethyl-2,3-dimethyl-cyclobutyl)-acetic acid;
(1α,2α,4α)-(1-Aminomethyl-2,4-dimethyl-cyclobutyl)-acetic acid;
[1R-(1α,2α,3β)]-(1-Aminomethyl-2,3-dimethyl-cyclobutyl)-acetic acid;
(1α,2α,4β)-(1-Aminomethyl-2,4-dimethyl-cyclobutyl)-acetic acid;
(1S-trans)-(1-Aminomethyl-2-methyl-cyclobutyl)-acetic acid;
[1S-(1α,2β,3β)]-(1-Aminomethyl-2,3-dimethyl-cyclobutyl)-acetic acid;
(1α,2β,4β)-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2β,4α)-(1-Aminomethyl-2,4-dimethyl-cyclobutyl)-acetic acid;
(1R-trans)-(1-Aminomethyl-2-methyl-cyclobutyl)-acetic acid;
[1R-(1α,2β,3β)]-(1-Aminomethyl-2,3-dimethyl-cyclobutyl)-acetic acid;
[1R-(1α,2β,4β)]-(1-Aminomethyl-2-ethyl-4-methyl-cyclobutyl)-acetic acid;
[1R-(1α,2β,3α)]-(1-Aminomethyl-2,3-dimethyl-cyclobutyl)-acetic acid;
(1α,2β,4α)-(1-Aminomethyl-2,4-dimethyl-cyclobutyl)-acetic acid;
(1S-cis)-(1-Aminomethyl-2-methyl-cyclobutyl)-acetic acid;
[1S-(1α,2α,3α)]-(1-Aminomethyl-2,3-dimethyl-cyclobutyl)-acetic acid;
[1S-(1α,2α,3α)]-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2α,4β)-(1-Aminomethyl-2,4-dimethyl-cyclobutyl)-acetic acid;
(3S,4S)-(1-Aminomethyl-3,4-dimethyl-cyclopentyl)-acetic acid;
(3R,4R)-(1-Aminomethyl-3,4-dimethyl-cyclopentyl)-acetic acid;
(3S,4S))-(1-Aminomethyl-3,4-diethyl-cyclopentyl)-acetic acid;
(3R,4R)-(1-Aminomethyl-3,4-diethyl-cyclopentyl)-acetic acid;
(3S,4S)-(1-Aminomethyl-3,4-diisopropyl-cyclopentyl)-acetic acid;
(3R,4R)-(1-Aminomethyl-3,4-diisopropyl-cyclopentyl)-acetic acid;
(3S,4S)-(1-Aminomethyl-3,4-di-tert-butyl-cyclopentyl)-acetic acid;
(3R,4R)-(1-Aminomethyl-3,4-di-tert-butyl-cyclopentyl)-acetic acid;
(3S,4S)-(1-Aminomethyl-3,4-diphenyl-cyclopentyl)-acetic acid;
(3R,4R)-(1-Aminomethyl-3,4-diphenyl-cyclopentyl)-acetic acid;
(3S,4S)-(1-Aminomethyl-3,4-dibenzyl-cyclopentyl)-acetic acid;
(3R,4R)-(1-Aminomethyl-3,4-dibenzyl-cyclopentyl)-acetic acid;
[1S-(1α,3α,4α)]-(1-Aminomethyl-3-methyl-4-ethyl-cyclopentyl)-acetic acid;
[1R-(1α,3β,4α)]-(1-Aminomethyl-3-methyl-4-ethyl-cyclopentyl)-acetic acid;
[1R-(1α,3α,4β)]-(1-Aminomethyl-3-methyl-4-ethyl-cyclopentyl)-acetic acid;
[1S-(1α,3β,4α)]-(1-Aminomethyl-3-methyl-4-ethyl-cyclopentyl)-acetic acid;
[1S-(1α,3α,4β)]-(1-Aminomethyl-3-methyl-4-isopropyl-cyclopentyl)-acetic acid;
[1R-(1α,3β,4α)]-(1-Aminomethyl-3-methyl-4-isopropyl-cyclopentyl)-acetic acid;
[1R-(1α,3α,4β)]-(1-Aminomethyl-3-methyl-4-isopropyl-cyclopentyl)-acetic acid;
[1S-(1α,3β,4α)]-(1-Aminomethyl-3-methyl-4-isopropyl-cyclopentyl)-acetic acid;
[1S-(1α,3α,4β)]-(1-Aminomethyl-3-methyl-4-tert-butyl-cyclopentyl)-acetic acid;
[1R-(1α,3β,4α)]-(1-Aminomethyl-3-methyl-4-tert-butyl-cyclopentyl)-acetic acid;

[1R-(1α,3α,4β)]-(1-Aminomethyl-3-methyl-4-tert-butyl-cyclopentyl)-acetic acid;
[1S-(1α,3β,4α)]-(1-Aminomethyl-3-methyl-4-tert-butyl-cyclopentyl)-acetic acid;
[1S-(1α,3α,4β)]-(1-Aminomethyl-3-methyl-4-phenyl-cyclopentyl)-acetic acid;
[1R-(1α,3β,4α)]-(1-Aminomethyl-3-methyl-4-phenyl-cyclopentyl)-acetic acid;
[1R-(1α,3α,4β)]-(1-Aminomethyl-3-methyl-4-phenyl-cyclopentyl)-acetic acid;
[1S-(1α,3β,4α)]-(1-Aminomethyl-3-methyl-4-phenyl-cyclopentyl)-acetic acid;
[1S-(1α,3α,4β)]-(1-Aminomethyl-3-benzyl-4-methyl-cyclopentyl)-acetic acid;
[1R-(1α,3β,4α)]-(1-Aminomethyl-3-benzyl-4-methyl-cyclopentyl)-acetic acid;
[1R-(1α,3α,4β)]-(1-Aminomethyl-3-benzyl-4-methyl-cyclopentyl)-acetic acid;
[1S-(1α,3β,4α)]-(1-Aminomethyl-3-benzyl-4-methyl-cyclopentyl)-acetic acid;
[1S-(1α,3α,4β)]-(1-Aminomethyl-3-ethyl-4-isopropyl-cyclopentyl)-acetic acid;
[1R-(1α,3β,4α)]-(1-Aminomethyl-3-ethyl-4-isopropyl-cyclopentyl)-acetic acid;
[1R-(1α,3α,4β)]-(1-Aminomethyl-3-ethyl-4-isopropyl-cyclopentyl)-acetic acid;
[1S-(1α,3β,4α)]-(1-Aminomethyl-3-ethyl-4-isopropyl-cyclopentyl)-acetic acid;
[1S-(1α,3α,4β)]-(1-Aminomethyl-3-tert-butyl-4-ethyl-cyclopentyl)-acetic acid;
[1R-(1α,3β,4α)]-(1-Aminomethyl-3-tert-butyl-4-ethyl-cyclopentyl)-acetic acid;
[1R-(1α,3α,4β)]-(1-Aminomethyl-3-tert-butyl-4-ethyl-cyclopentyl)-acetic acid;
[1S-(1α,3β,4α)]-(1-Aminomethyl-3-tert-butyl-4-ethyl-cyclopentyl)-acetic acid;
[1S-(1α,3α,4β)]-(1-Aminomethyl-3-ethyl-4-phenyl-cyclopentyl)-acetic acid;
[1R-(1α,3β,4α)]-(1-Aminomethyl-3-ethyl-4-phenyl-cyclopentyl)-acetic acid;
[1R-(1α,3α,4β)]-(1-Aminomethyl-3-ethyl-4-phenyl-cyclopentyl)-acetic acid;
[1S-(1α,3β,4α)]-(1-Aminomethyl-3-ethyl-4-phenyl-cyclopentyl)-acetic acid;
[1S-(1α,3α,4β)]-(1-Aminomethyl-3-benzyl-4-ethyl-cyclopentyl)-acetic acid;
[1R-(1α,3β,4α)]-(1-Aminomethyl-3-benzyl-4-ethyl-cyclopentyl)-acetic acid;
[1R-(1α,3α,4β)]-(1-Aminomethyl-3-benzyl-4-ethyl-cyclopentyl)-acetic acid;
[1S-(1α,3β,4α)]-(1-Aminomethyl-3-benzyl-4-ethyl-cyclopentyl)-acetic acid;
[1S-(1α,3α,4β)]-(1-Aminomethyl-3-tert-butyl-4-isopropyl-cyclopentyl)-acetic acid;
[1R-(1α,3β,4α)]-(1-Aminomethyl-3-tert-butyl-4-isopropyl-cyclopentyl)-acetic acid;
[1R-(1α,3α,4β)]-(1-Aminomethyl-3-tert-butyl-4-isopropyl-cyclopentyl)-acetic acid;
[1S-(1α,3β,4α)]-(1-Aminomethyl-3-tert-butyl-4-isopropyl-cyclopentyl)-acetic acid;
[1S-(1α,3α,4β)]-(1-Aminomethyl-3-isopropyl-4-phenyl-cyclopentyl)-acetic acid;
[1R-(1α,3β,4α)]-(1-Aminomethyl-3-isopropyl-4-phenyl-cyclopentyl)-acetic acid;
[1R-(1α,3α,4β)]-(1-Aminomethyl-3-isopropyl-4-phenyl-cyclopentyl)-acetic acid;
[1S-(1α,3β,4α)]-(1-Aminomethyl-3-isopropyl-4-phenyl-cyclopentyl)-acetic acid;
[1S-(1α,3α,4β)]-(1-Aminomethyl-3-benzyl-4-isopropyl-cyclopentyl)-acetic acid;
[1R-(1α,3β,4α)]-(1-Aminomethyl-3-benzyl-4-isopropyl-cyclopentyl)-acetic acid;
[1R-(1α,3α,4β)]-(1-Aminomethyl-3-benzyl-4-isopropyl-cyclopentyl)-acetic acid;
[1S-(1α,3β,4α)]-(1-Aminomethyl-3-benzyl-4-isopropyl-cyclopentyl)-acetic acid;
[1S-(1α,3α,4β)]-(1-Aminomethyl-3-tert-butyl-4-phenyl-cyclopentyl)-acetic acid;
[1R-(1α,3β,4α)]-(1-Aminomethyl-3-tert-butyl-4-phenyl-cyclopentyl)-acetic acid;
[1R-(1α,3α,4β)]-(1-Aminomethyl-3-tert-butyl-4-phenyl-cyclopentyl)-acetic acid;
[1S-(1α,3β,4α)]-(1-Aminomethyl-3-tert-butyl-4-phenyl-cyclopentyl)-acetic acid;
[1R-(1α,3α,4β)]-(1-Aminomethyl-3-benzyl-4-tert-butyl-cyclopentyl)-acetic acid;
[1S-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-tert-butyl-cyclopentyl)-acetic acid;
[1R-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-phenyl-cyclopentyl)-acetic acid;
[1R-(1α,3β,4α)]-(1-Aminomethyl-3-benzyl-4-phenyl-cyclopentyl)-acetic acid;
[1R-(1α,3α,4β)]-(1-Aminomethyl-3-benzyl-4-phenyl-cyclopentyl)-acetic acid;
[1S-(1α,3β,4α)]-(1-Aminomethyl-3-benzyl-4-phenyl-cyclopentyl)-acetic acid;
(1R-cis)-(1-Aminomethyl-2-methyl-cyclopentyl)-acetic acid;
(1S-cis)-(1-Aminomethyl-2-methyl-cyclopentyl)-acetic acid;
(1R-trans)-(1-Aminomethyl-2-methyl-cyclopentyl)-acetic acid;
(1S-trans)-(1-Aminomethyl-2-methyl-cyclopentyl)-acetic acid;
(R)-(1-Aminomethyl-2,2-dimethyl-cyclopentyl)-acetic acid;
(S)-(1-Aminomethyl-2,2-dimethyl-cyclopentyl)-acetic acid;
(1-Aminomethyl-2,2,5,5-tetramethyl-cyclopentyl)-acetic acid;
(1α,2β,5β)-(1-Aminomethyl-2,5-dimethyl-cyclopentyl)-acetic acid;
(2R, 5R)-(1-Aminomethyl-2,5-dimethyl-cyclopentyl)-acetic acid;
(2S. 5S)-(1-Aminomethyl-2,5-dimethyl-cyclopentyl)-acetic acid;
(1α,2α,5α)-(1-Aminomethyl-2,5-dimethyl-cyclopentyl)-acetic acid;
[1R-(1α,2α,3α)]-(1-Aminomethyl-2,3-dimethyl-cyclopentyl)-acetic acid;
[1R-(1α,2β,3α)]-(1-Aminomethyl-2,3-dimethyl-cyclopentyl)-acetic acid;
[1R-(1α,2α,3β)]-(1-Aminomethyl-2,3-dimethyl-cyclopentyl)-acetic acid;
[1R-(1α,2β,3β)]-(1-Aminomethyl-2,3-dimethyl-cyclopentyl)-acetic acid;
[1S-(1α,2α,3α)]-(1-Aminomethyl-2,3-dimethyl-cyclopentyl)-acetic acid;
[1S-(1α,2β,3α)]-(1-Aminomethyl-2,3-dimethyl-cyclopentyl)-acetic acid;
[1S-(1α,2α,3β)]-(1-Aminomethyl-2,3-dimethyl-cyclopentyl)-acetic acid;
[1S-(1α,2β,3β)]-(1-Aminomethyl-2,3-dimethyl-cyclopentyl)-acetic acid;

[1R-(1α,2α,4α)]-(1-Aminomethyl-2,4-dimethyl-cyclopentyl)-acetic acid;
[1S-(1α,2α,4α)]-(1-Aminomethyl-2,4-dimethyl-cyclopentyl)-acetic acid;
[1R-(1α,2α,4β)]-(1-Aminomethyl-2,4-dimethyl-cyclopentyl)-acetic acid;
[1S-(1α,2α,4β)]-(1-Aminomethyl-2,4-dimethyl-cyclopentyl)-acetic acid;
[1R-(1α,2α,4α)]-(1-Aminomethyl-2,4-dimethyl-cyclopentyl)-acetic acid;
[1S-(1α,2β,4α)]-(1-Aminomethyl-2,4-dimethyl-cyclopentyl)-acetic acid;
[1R-(1α,2β,4β)]-(1-Aminomethyl-2,4-dimethyl-cyclopentyl)-acetic acid; and
[1S-(1α,2β,4β)]-(1-Aminomethyl-2,4-dimethyl-cyclopentyl)-acetic acid.

Certain intermediates are useful in the preparation of the compounds of the invention:
(trans)-(3,4-Dimethyl-cyclopentylidene)-acetic acid ethyl ester;
(trans)-(3,4-Dimethyl-1-nitromethyl-cyclopentyl)-acetic acid;
(±)-(trans)-7,8-Dimethyl-spiro[4.4]nonane-2-one;
(1-Nitromethyl-cyclobutyl)-acetic acid ethyl ester;
(cis/trans)-(3R)-(3-Methyl-1-nitromethyl-cyclopentyl)-acetic acid ethyl ester;
(cis/trans)-(7R)-7-Methyl-spiro[4.4]nonane-2-one;
(cis)-(3,4-Dimethyl-cyclopentyldiene)-acetic acid ethyl ester:
(trans)-3,4-Dimethyl-1-nitromethyl-cyclopentyl)-acetic acid ethyl ester;
(trans)-7,8-Dimethyl-spiro[4.4]nonane-2-one;
(3-Benzyl-cyclobutylidene)-acetic acid ethyl ester; and
(cis/trans)-(3-Benzyl-1-nitromethyl-cyclopentyl)-acetic acid ethyl ester.

The term "lower alkyl" is a straight or branched group of from 1 to 4 carbons.

The term "alkyl" is a straight or branched group of from 1 to 6 carbon atoms including but not limited to methyl, ethyl, propyl, n-propyl, isopropyl, butyl, 2-butyl, tert-butyl, pentyl, except as where otherwise stated.

The benzyl and phenyl groups may be unsubstituted or substituted by from 1 to 3 substituents selected from hydroxy, carboxy, carboalkoxy, halogen, $CF_3$, nitro, alkyl, and alkoxy. Preferred are halogens.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the-scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

Methods and Materials

Animals

Male Sprague-Dawley rats (180–250 g) were obtained from Bantin and Kingman, (Hull, U.K.). Animals were housed in groups of 6 to 10 under a 12 hour light/dark cycle (lights on at 7 hours, 0 minutes) with food and water ad libitum.

Carrageenan-induced Thermal Hyperalgesia in the Rat

Thermal hyperalgesia was assessed using the rat plantar test (Ugo Basile, Italy) following a modified method of Hargreaves, et al., 1988. Rats were habituated to the apparatus which consisted of three individual perspex boxes on an elevated glass table. A mobile radiant heat source located under the table was focused onto the desired paw and paw withdrawal latencies (PWL) recorded. PWL were taken 3 times for both hind paws of each animal, the mean of which represented baselines for right and left hind paws. At least 5 minutes were allowed between each PWL for an animal. The apparatus was calibrated to give a PWL of approximately 10 s. There was an automatic cutoff point of 20 s to prevent tissue damage. After baseline PWLs were determined, animals received an intraplantar injection of carrageenan (100 μL of 20 mg/mL) into the right hind paw. PWLs were reassessed following the same protocol as above 2-hour post-carrageenan (this time point represented the start of peak hyperalgesia) to ascertain that hyperalgesia had developed. Test compounds were administered orally (in a volume of 1 mL/kg) at 2.5 hours after carrageenan. PWLs were reassessed at various times after drug administration.

A Model of Anticonvulsant Efficacy and Protocol for DBA2 Test: Prevention of Audiogenic Seizures in DBA/2 Mice Methods All procedures were carried out in compliance with the NI/H Guide for the Care and Use of Laboratory Animals under a protocol approved by the Parke-Davis Animal Use Committee. Male DBA/2 mice, 3 to 4 weeks old, were obtained from Jackson Laboratories, Bar Harbour, Me. Immediately before anticonvulsant testing, mice were placed upon a wire mesh, 4 inches square suspended from a steel rod. The square was slowly inverted through 180 degrees and mice observed for 30 seconds. Any mouse falling from the wire mesh was scored as ataxic.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 seconds) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. compounds that are insoluble will be suspended in 1% carboxymethocellulose. Doses are expressed as weight of the active drug moiety.

Results

The dose-dependent suppression of sound-induced tonic seizures in DBA/2 mice was tested, and the corresponding $ED_{50}$ values are shown in Table 1.

The present results show that the compounds of the invention given orally cause dose-related anticonvulsant effects in a sound susceptible strain (DBA/2) of mice, confirming previous data showing anticonvulsant activity in other models of experimental epilepsy. The effective dosages of drugs in this model are lower than those in the maximal electroshock test, confirming that DBA/2 mice are a sensitive model for detecting anticonvulsant actions.

TABLE 1

| Compound | Structure | $IC_{50}$ (μM) at $\alpha_2\delta$ binding site | Carrageenan Induced Thermal Hyperalgesia in the Rat | | DBA/2 Audiogenic Mouse |
| --- | --- | --- | --- | --- | --- |
| | | | % MPE[a] 1 hr postdose @ 30 mg/kg PO | % MPE[a] 2 hr postdose @ 30 mg/kg PO | % Protected 1 hr postdose 30 mg/kg PO |
| (±)-(trans)-(1-Aminomethyl-3,4-dimethyl-cyclopentyl)-acetic acid hydrochloride | | 0.034 | 23 | 72 | 100 |
| (+)-(trans)-(1-Aminomethyl-3,4-dimethyl-cyclopentyl)-acetic acid hydrochloride | | 0.022 | 109 | 118 | 100 |
| (−)-(trans)-(1-Aminomethyl-3,4-dimethyl-cyclopentyl)-acetic acid hydrochloride | | 1.0 | | | |
| (cis/trans)-(3R)-(1-Aminomethyl-3-methyl-cyclopentyl)-acetic acid hydrochloride | | 0.088 | 67 | 53 | 100 |
| (trans)-(1-Aminomethyl-3,4-dimethyl-cyclopentyl)-acetic acid hydrochloride | | 0.154 | −7 | −2 | 100 |
| (1-Aminomethyl-cyclobutyl)-acetic acid hydrochloride | | 0.598 | 4 | 4 | 20 (2 hour postdose) |

TABLE 1-continued

| Compound | Structure | IC$_{50}$ ($\mu$M) at $\alpha_2\delta$ binding site | Carrageenan Induced Thermal Hyperalgesia in the Rat | | DBA/2 Audiogenic Mouse |
|---|---|---|---|---|---|
| | | | % MPE[a] 1 hr postdose @ 30 mg/kg PO | % MPE[a] 2 hr postdose @ 30 mg/kg PO | % Protected 1 hr postdose 30 mg/kg PO |
| (cis/trans)-(1-Aminomethyl-3-benzyl-cyclobutyl)-acetic acid hydrochloride | 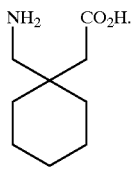 | >10 | 0 | 0 | not tested |

[a]MPE: maximum possible effect - set as baseline value prior to treatment with carrageenan.

The radioligand binding assay using [³H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel", Gee N. et al., *J. Biological Chemistry*, in press).

The compounds of the invention show good binding affinity to the $\alpha_2\delta$ subunit. Gabapentin (Neurontin®) is about 0.10 to 0.12 $\mu$M in this assay. Since the compounds of the instant invention also bind to the subunit, they are expected to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)-cyclohexaneacetic acid of structural formula

NH₂   CO₂H.

The compounds of the invention are also expected to be useful in the treatment of epilepsy.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular accident (CVA) and includes acute thromboembolic stroke. Stroke includes both focal and global ischemia. Also, included are transient cerebral ischemic snacks and other cerebral vascular probleems accompanied by cerebral ischemia such as in a patient undergoing carotid endarterectomy specificaUy or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems that GABA-mimetics will decrease or inhibit cerebral function and will therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

Material and Methods

Carrageenin-Induced Hyperalgesia

Nociceptive pressure thresholds were measured in the rat paw pressure test using an analgesymeter (Randall-Sellitto Method: Randall L. O., Sellitto J. J., A method for measurement of analgesic activity on inflamed tissue. *Arch. Int. Pharmacodyn.*, 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 $\mu$L of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post-carrageenin.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2.0 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (*Callithrix Jacchus*) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 1989;28:901–905).

Rat Elevated X-Maze

A standard elevated X-maze (Handley S. L., et al., Effects of alpha-adrenoceptor agonists and antagonists in a maze-exploration model of 'fear'—motivated behavior. *Naunyn-Schiedeberg's Arch. Pharmacol.*, 1984;327:1–5) was automated as previously described (Field, et al., Automation of the rat elevated X-maze test of anxiety. *Br. J. Pharmacol.*, 1991;102(Suppl):304P). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 1989;96(Suppl):312P).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 1995;5:7–9).

The compounds of the instant invention are also expected to be useful in treating the symptoms of manic, acute or chronic, single upside, or recurring. They are also expected to be useful in treating and/or preventing bipolar disorder (U.S. Pat. No. 5,510,381).

Models of Irritable Bowel Syndrome

TNBS-Induced Chronic Visceral Allodynia in Rats

Injections of trinitrobenzene sulfonic acid (TNBS) into the colon have been found to induce chronic colitis, In humans, digestive disorders are often associated with visceral pain. In these pathologies, the visceral pain threshold is decreased indicating a visceral hypersensitivity. Consequently, this study was designed to evaluate the effect of injection of TNBS into the colon on visceral pain threshold in an experimental model of colonic distension.

Materials and Methods

Animals and Surgery

Male Sprague-Dawley rats (Janvier, Le Genest-St-Ilse, France) weighing 340–400 g are used. The animals are housed 3 per cage in a regulated environment (20±1° C., 50±5% humidity, with light 8:00 am to 8:00 pm). Under anesthesia (ketamine 80 mg/kg i.p; acepromazin 12 mg/kg ip), the injection of TNBS (50 mg/kg) or saline (1.5 mL/kg) is performed into the proximal colon (1 cm from the cecum). After the surgery, animals are individually housed in polypropylene cages and kept in a regulated environment (20±1° C., 50±5% humidity, with light 8:00 am to 8:00 pm) during 7 days.

Experimental Procedure

At Day 7 after TNBS administration, a balloon (5–6 cm length) is inserted by anus and kept in position (tip of balloon 5 cm from the anus) by taping the catheter to the base of the tail. The balloon is progressively inflated by step of 5 mm Hg, from 0 to 75 mm Hg, each step of inflation lasting 30 seconds. Each cycle of colonic distension is controlled by a standard barostat (ABS, St-Dié, France). The threshold corresponds to the pressure which produced the first abdominal contraction and the cycle of distension is then discontinued. The colonic threshold (pressure expressed in mm Hg) is determined after performance of four cycles of distension on the same animal.

Determination of the Activity of the Compound

Data is analyzed by comparing test compound (1-treated group with TNBS-treated group and control group. Mean and sem are calculated for each group. The antiallodynic activity of the compound is calculated as follows:

Activity(%)=(group C−group T)/(group A−group T)

Group C: mean of the colonic threshold in the control group

Group T: mean of the colonic threshold in the TNBS-treated group

Group A: mean of the colonic threshold in the test compound-treated group

Statistical Analysis

Statistical significance between each group was determined by using a one-way ANOVA followed by Student's unpaired t-test. Differences were considered statistically significant at $p<0.05$.

Compounds

TNBS is dissolved in EtOH 30% and injected under a volume of 0.5 mL/rat. TNBS is purchased from Fluka.

Oral administration of the test compound or its vehicle is performed 1 hour before the colonic distension cycle.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or 1A or a corresponding pharmaceutically acceptable salt of a compound of Formula 1 or 1A.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

General Synthetic Schemes
Compounds

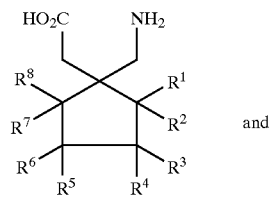

and

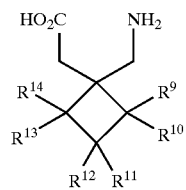

wherein $R^1$–$R^{14}$ may be selected independently from: hydrogen, straight or branched alkyl of from 1 to 6 carbon atoms, phenyl, benzyl, fluorine, chlorine, bromine, hydroxy, hydroxymethyl, amino, aminomethyl, trifluoromethyl, —$OR^{15}$, where $R^{15}$ may be straight or branched alkyl of from 1 to 6 carbon atoms, phenyl or benzyl, —$CO_2H$, $CO_2R^{15}$, —$CH_2CO_2H$, —$CH_2CO_2R^{15}$. $R^1$–$R^8$ may not hydrogen can be made by the following methods.

Both the 4- and 5-membered ring compounds may be synthesized by the routes outlined below for the 5-membered ring system. The compounds claimed may be synthesized, for example, by utilizing the general strategy (General Scheme 1) outlined by G. Griffiths et al., *Helv. Chim. Acta*, 1991;74:309. Alternatively, they may also be made as shown (General Scheme 2), analogously to the published procedure for the synthesis of 3-oxo-2,8-diazaspiro[4,5]decane-8-carboxylic acid tert-butyl ester (P. W. Smith et al., *J. Med. Chem.*, 1995;38:3772). The compounds may also be synthesized by the methods outlined by G. Satzinger et al., (Ger Offen U.S. Pat. No. 2,460,891; U.S. Pat. No. 4,024,175, and Ger Offen U.S. Pat. No. 2,611,690; U.S. Pat. No. 4,152,326) (General Schemes 3 and 4). The compounds may also be synthesized by the route outlined by G. Griffiths et al., *Helv. Chim. Acta*, 1991;74:309 (General Scheme 5).

General Scheme 1

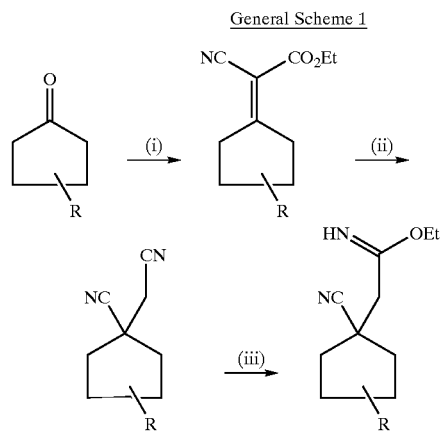

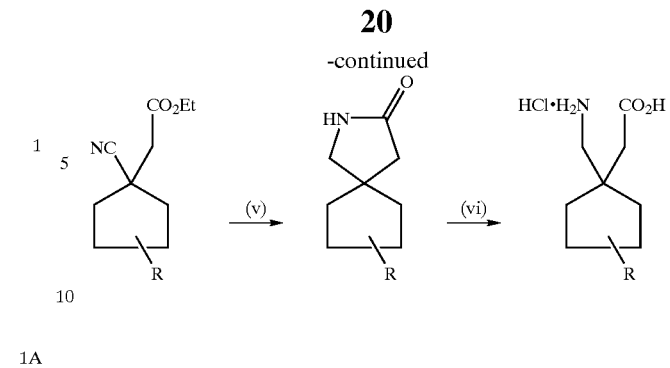

(i) Ethyl cyanoacetate, piperidine (Cope et al., *J. Am. Chem. Soc.*, 1941;63:3452); (ii) NaCN, EtOH/$H_2O$; (iii) EtOH, HCl; (iv) $H_2O/H^+$; (v) $H_2$, Rh/C, MeOH; (vi) HCl.

General Scheme 2

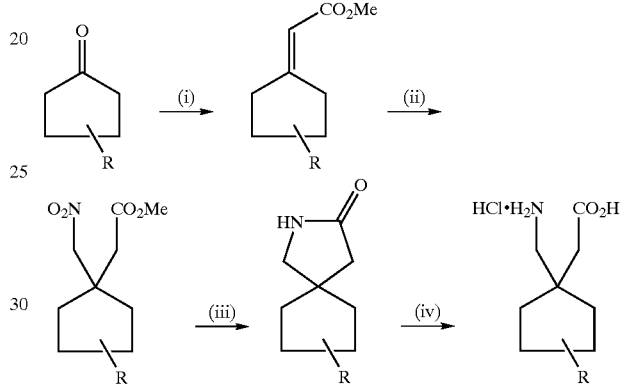

(i) $Ph_3P=CHCO_2Me$; (ii) $MeNO_2$, 1,1,3,3-tetramethylguanidine; (iii) Raney nickel, EtOH/$H_2O$; (iv) HCl.

General Scheme 3

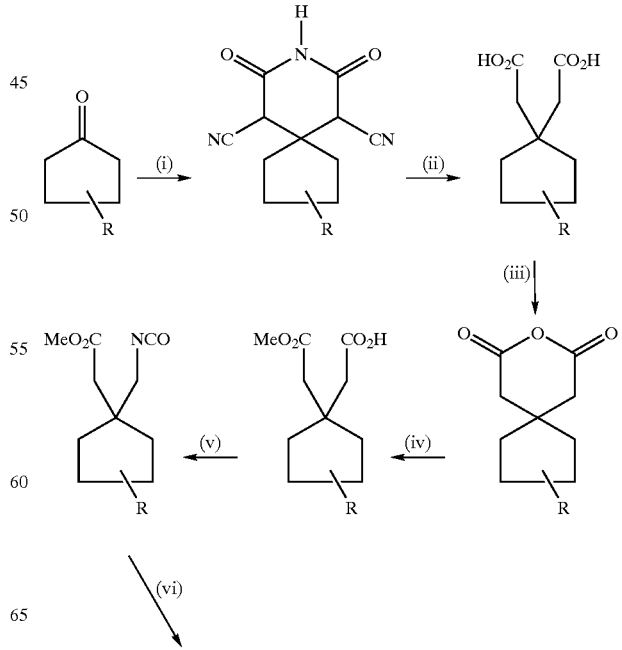

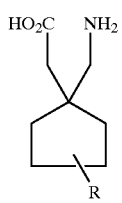

(i) Ethylcyanoacetate, ammonia then $H_3O^+$; (ii) $H_2SO_4$; (iii) $Ac_2O$; (iv) MeOH; (v) Curtius Reaction; (vi) HCl, $H_2O$ then anion exchange.

General Scheme 4

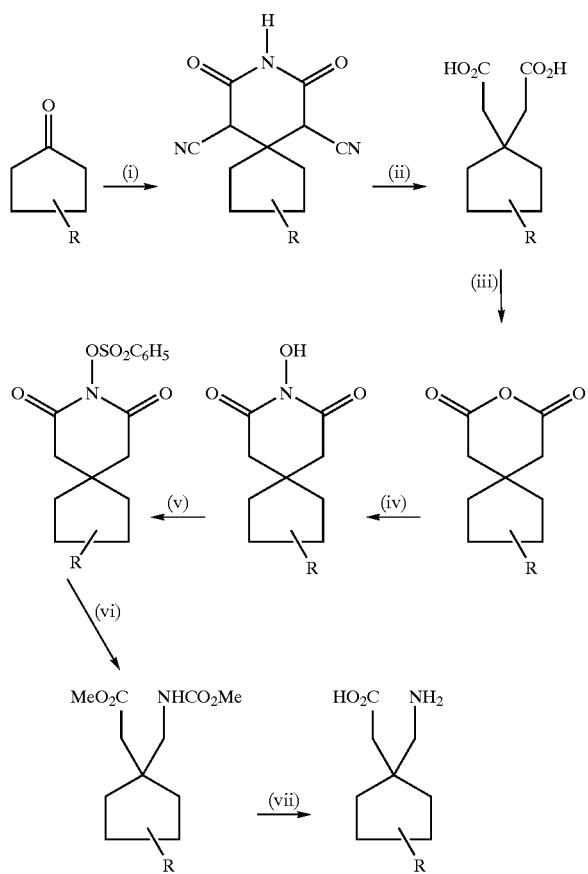

(i) Ethylcyanoacetate, ammonia then $H_3O^+$; (ii) $H_2SO_4$; (iii) $Ac_2O$; (iv) $H_2NOH$; (v) $PhSO_2Cl$; (vi) $Et_3N$, MeOH; (vii) HCl, $H_2O$ then anion exchange.

General Scheme 5

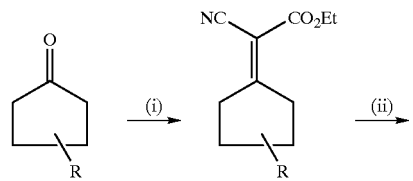

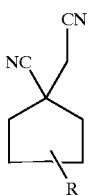

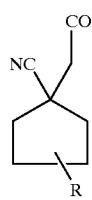

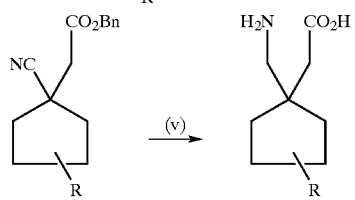

(i) Ethyl cyanoacetate, piperidine (Cope et al., *J. Am. Chem. Soc.*, 1941;63:3452); (ii) NaCN, EtOH/$H_2O$; (iii) BnOH, HCl; (iv) $H_2O/H^+$; (v) $H_2$, Rh/C, MeOH.

The following examples are illustrative of the instant invention; they are not intended to limit the scope.

In Examples 1 to 8, the first step involves the conversion of a cyclic ketone to an α,β-unsaturated ester 2 via use of a trialkylphosphonoacetate or an (alkoxycarbonylmethyl) triphenylphosphonium halide and a base, such as sodium hydride, potassium hydride, lithium- or sodium- or potassium-hexamethyldisilazide, butyllithium or potassium t-butoxide in a solvent such as tetrahydrofuran, dimethylformamide, diethylether or dimethylsulfoxide at a suitable temperature in the range from −78° C. to 100° C.

The second step involves reaction of the α,β-unsaturated ester 2 with nitromethane and a suitable base such as tetrabutylammonium fluoride, tetramethylguanidine, 1,5-diazabicyclo[4,3,0]non-5-ene, 1,8-diazabicyclo[5,4,0]undec-7-ene, a sodium or potassium alkoxide, sodium hydride or potassium fluoride in a solvent such as tetrahydrofuran, diethylether, dimethylformamide, dimethylsulphoxide, benzene, toluene, dichloromethane, chloroform or tetrachloromethane at a suitable temperature in the range from −20° C. to 100° C.

The third step involves catalytic hydrogenation of the nitro moiety of 3 using a catalyst such as Raney nickel, palladium on charcoal or rhodium catalyst or other nickel or palladium containing catalyst in a solvent such as methanol, ethanol, isopropanol, ethyl acetate, acetic acid, 1,4-dioxane, chloroform or diethyl ether at a suitable temperature in the range from 20° C. to 80° C.

The fourth step involves hydrolysis of lactam 4 using hydrochloric acid and may also utilize a co-solvent such tetrahydrofuran or 1,4-dioxane or other such inert water miscible solvent at a suitable temperature in the range from 20° C. to reflux.

EXAMPLE 1

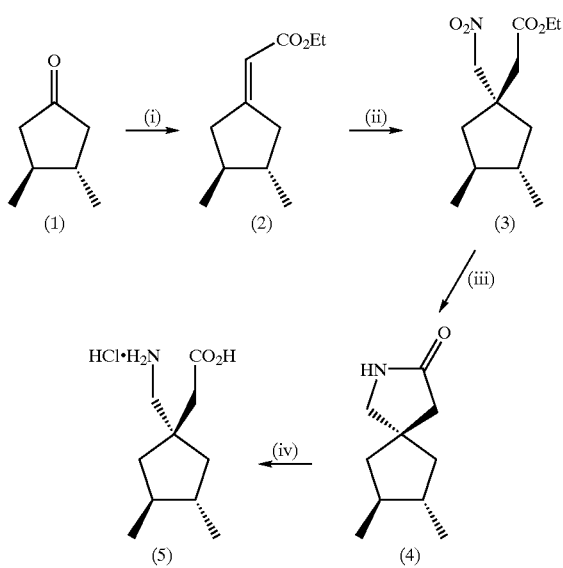

Reagents: (i) Triethylphosphonoacetate, NaH; (ii) MeNO$_2$, Bu$_4$N$^+$F$^-$; (iii) H$_2$, Ni; (iv) HCl

Synthesis of (trans)-(3,4-Dimethyl-cyclopentylidene)-acetic acid ethyl ester (2)

NaH (60% dispersion in oil, 737 mg, 18.42 mmol) was suspended in dry tetrahydrofuran (50 mL) and cooled to 0° C. Triethylphosphonoacetate (3.83 mL, 19.30 mmol) was added and the mixture stirred at 0° C. for 15 minutes. The ketone (1) (1.965 g, 17.54 mmol) in TBF (10 mL) was then added and the mixture allowed to warm to room temperature. After 2 hours, the mixture was partitioned between diethyl ether (200 mL) and water (150 mL). The organic phase was separated, washed with brine, dried (MgSO$_4$) and the solvent removed in vacuo. The residue was purified by flash chromatography (silica, ethyl acetate:heptane 1:9) to give 3.01 g (94%) of (2) as a colorless oil.

$^1$H NMR 400 MHz (CDCl$_3$): δ 1.01 (3H, d, J=6 Hz), 1.03 (3H, d, J=6 Hz), 1.26 (3H, t, J=7 Hz), 1.49 (2H, m), 2.07 (1H, m), 2.24 (1H, m), 2.61 (1H, m), 4.13 (2H, q, J=7 Hz), 5.72 (1H, s).

MS (CI+) m/e: 183 ([MH$^+$], 18%).

Synthesis of (trans)-(3,4-Dimethyl-1-nitromethyl-cyclopentyl)-acetic acid ethyl ester (3)

The unsaturated ester (2) (2.95 g, 16.2 mmol) was dissolved in tetrahydrofuran (10 mL) and stirred at 70° C. with nitromethane (1.9 mL, 35.2 mmol) and tetrabutylammonium fluoride (1.0 M in tetrahydrofuran, 22 mL, 22.0 mmol). After 6 hours, the mixture was cooled to room temperature, diluted with ethyl acetate (50 mL), and washed with 2N HCl (30 mL) followed by brine (50 mL). The organic phase was collected, dried (MgSO$_4$) and the solvent removed in vacuo. The residue was purified by flash chromatography (silica, ethyl acetate:heptane 1:9) to give 1.152 g (29%) of a clear oil.

$^1$H NMR 400 MHz (CDCl$_3$): δ 0.98 (6H, d, J=6 Hz), 1.10–1.39 (5H, m), 1.47 (2H, m), 1.87 (1H, m), 2.03 (1H, m), 2.57 (2H, ABq, J=16, 38 Hz), 4.14 (2H, q, J=7 Hz), 4.61 (2H, ABq, J=12, 60 Hz).

MS (ES+) m/e: 244 ([MH$^+$], 8%).

IR (film) ν cm$^{-1}$: 1186, 1376, 1549, 1732, 2956.

Synthesis of (±)-(trans)-7,8-Dimethyl-spiro[4.4]nonan-2-one (4)

The nitroester (3) (1.14 g, 4.7 mmol) was dissolved in methanol (50 mL) and shaken over Raney nickel catalyst under an atmosphere of hydrogen (40 psi) at 30° C. After 5 hours, the catalyst was removed by filtration through celite. The solvent was removed in vacuo to give 746 mg (95%) of a pale yellow oil which solidified on standing.

$^1$H NMR 400 MHz (CDCl$_3$): δ 0.98 (6H, d, J=6 Hz), 1.32 (2H, m), 1.46 (2H, m), 1.97 (2H, m), 2.27 (2H, ABq, J=16, 27 Hz), 3.23 (2H, s), 5.62 (1H, br s).

MS (ES+) m/e: 168 ([MH$^+$], 100%).

IR (film) ν cm$^{-1}$: 1451, 1681, 1715, 2948, 3196.

Synthesis of (±)-(trans)-(1-Aminomethyl-3,4-dimethyl-cyclopentyl)-acetic acid hydrochloride (5)

The lactam (4) (734 mg, 4.40 mmol) was heated to reflux in a mixture of 1,4-dioxan (5 mL) and 6N HCl (15 mL). After 4 hours, the mixture was cooled to room temperature, diluted with water (20 mL), and washed with dichloromethane (3×30 mL). The aqueous phase was collected and the solvent removed in vacuo. The residue was triturated with ethyl acetate to give 675 mg (69%) of a white solid after collection and drying.

$^1$H NMR 400 MHz (d$_6$-DMSO): δ 0.91 (6H, d, J=6 Hz), 1.18 (2H, m), 1.42 (2H, m), 1.72 (1H, m), 1.87 (1H, m), 2.42 (2H, ABq, J=16, 24 Hz), 2.90 (2H, ABq, J=12, 34 Hz), 8.00 (3H, br s), 12.34 (1H, br s).

MS (ES+) m/e: 186 ([MH-HCl]$^+$, 100%).

EXAMPLE 2

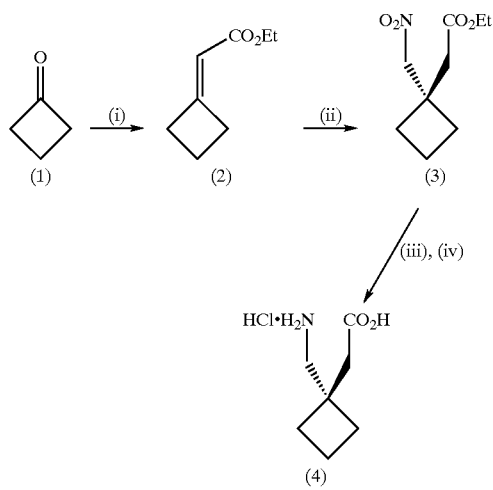

Reagents: (i) Triethylphosphonoacetate, NaH; (ii) MeNO$_2$, Bu$_4$N$^+$F$^-$; (iii) H$_2$, Ni; (iv) HCl

Synthesis of Cyclobutylidene-acetic acid ethyl ester (2)

NaH (60% dispersion in oil, 1.80 g, 44.94 mmol) was suspended in dry tetrahydrofuran (80 mL) and cooled to 0° C. Triethylphosphonoacetate (9.33 mL, 47.08 mmol) was added and the mixture stirred at 0° C. for 15 minutes.

Cyclobutanone (1) (3.0 g, 42.8 mmol) in THF (20 mL) was then added and the mixture allowed to warm to room temperature. After 2 hours, the mixture was partitioned between diethyl ether (200 mL) and water (150 mL). The organic phase was separated, washed with brine, dried (MgSO$_4$), and the solvent removed in vacuo at 600 mm Hg. The residue was purified by flash chromatography (silica, ethyl acetate:pentane 1:19) to give 5.81 g (96%) of (2) as a colorless oil.

$^1$H NMR, 400 MHz (CDCl$_3$): δ 1.27 (3H, t, J=6 Hz), 2.09 (2H, m), 2.82 (2H, m), 3.15 (2H, m), 4.14 (2H, q, J=6 Hz), 5.58 (1H, s).

MS (ES+) m/e: 141 ([MH$^+$], 100%). IR (film) ν cm$^{-1}$: 1088, 1189, 1336, 1673, 1716, 2926.

Synthesis of (1-Nitromethyl-cyclobutyl)-acetic acid ethyl ester (3)

The unsaturated ester (2) (5.79 g, 41.4 mmol) was dissolved in tetrahydrofuran (20 mL) and stirred at 70° C. with nitromethane (4.67 mL, 86.4 mmol) and tetrabutylammonium fluoride (1.0 M in tetrahydrofuran, 55 mL, 55.0 mmol). After 18 hours, the mixture was cooled to room temperature, diluted with ethyl acetate (150 mL), and washed with 2N HCl (60 mL) followed by brine (100 mL). The organic phase was collected, dried (MgSO$_4$), and the solvent removed in vacuo. The residue was purified by flash chromatography (silica, ethyl acetate:heptane 1:1) to give 4.34 g (52%) of a clear oil.

$^1$H NMR 400 MHz (CDCl$_3$): δ 1.27 (3H, t, J=6 Hz), 1.96–2.20 (6H, m), 2.71 (2H, s), 4.15 (2H, q, J=6 Hz), 4.71 (2H, s).

MS (ES+) m/e: 202 ([MH$^+$], 100%).

IR (film) ν cm$^{-1}$: 1189, 1378, 1549, 1732, 2984.

Synthesis of (1-Aminomethyl-cyclobutyl)-acetic acid hydrochloride (4)

The nitroester (3) (2.095 g, 10.4 mmol) was dissolved in methanol (50 mL) and shaken over Raney nickel catalyst under an atmosphere of hydrogen (45 psi) at 30° C. After 6 hours, the catalyst was removed by filtration through celite. The solvent was removed in vacuo to give 1.53 g of a pale yellow oil which was used without purification. The oil was dissolved in 1,4-dioxane (5 mL) and 6N HCl (15 mL) and heated to reflux. After 5 hours, the mixture was cooled to room temperature, diluted with water (20 mL), and washed with dichloromethane (3×30 mL). The aqueous phase was collected and the solvent removed in vacuo. The residue was triturated with ethyl acetate to give 1.35 g (72%) of a white solid after collection and drying.

$^1$H NMR 400 MHz (d$_6$-DMSO): δ 1.80–2.03 (6H, m), 2.59 (2H, s), 3.02 (2H, s) 8.04 (3H, br s), 12.28 (1H, br s).

MS (ES+) m/e: 144 ([MH-HCl]$^+$, 100%).

Microanalysis calculated for C$_7$H$_{14}$NO$_2$Cl: C, 46.80%; H, 7.86%; N, 7.80%. Found: C, 46.45%; H, 7.98%; N, 7.71%.

EXAMPLE 3

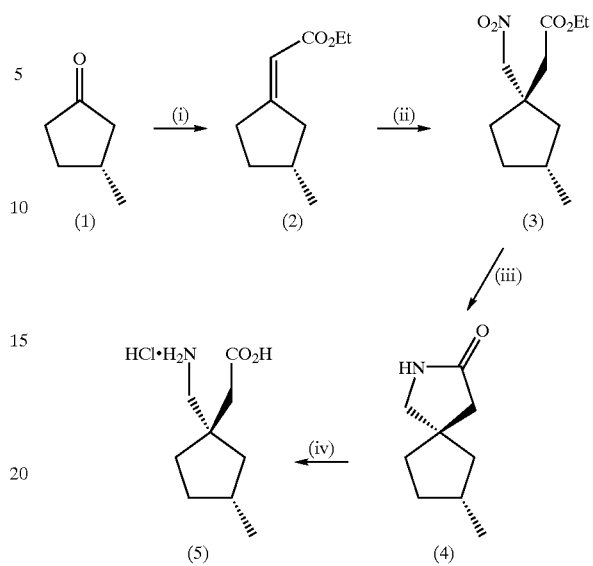

Reagents: (i) Triethylphosphonoacetate, NaH; (ii) MeNO$_2$, Bu$_4$N$^+$F$^-$; (iii) H$_2$, Ni; (iv) HCl Synthesis of (R)-(3-Methyl-cyclopentylidene)-acetic acid ethyl ester (2)

NaH (60% dispersion in oil, 1.86 g, 46.5 mmol) was suspended in dry tetrahydrofuran (40 mL) and cooled to 0° C. Triethylphosphonoacetate (9.69 mL, 48.8 mmol) was added and the mixture stirred at 0° C. for 15 minutes. The ketone (1) (5 ml, 46.5 mmol) in THF (10 mL) was then added and the mixture allowed to warm to room temperature. After 2 hours, the mixture was partitioned between diethyl ether (200 mL) and water (150 mL). The organic phase was separated, washed with brine, dried (MgSO$_4$) and the solvent removed in vacuo. The residue was purified by flash chromatography (silica, ethyl acetate:heptane 1:9) to give 5.45 g (70%) of (2) as a colorless oil.

$^1$H NMR 400 MHz (CDCl$_3$): δ 1.04 (3H, m), 1.27 (3H, t, J=7 Hz), 1.80–2.74 (7H, m), 2.90–3.15 (1H, m), 4.13 (2H, q, J=7 Hz), 5.76 (1H, s).

MS (CI+) m/e: 169 ([MH$^+$], 20%).

IR (film) ν cm$^{-1}$: 1205, 1371, 1653, 1716, 2955.

Synthesis of (cis/trans)-(3R)-(3-Methyl-1-nitromethyl-cyclopentyl)-acetic acid ethyl ester (3)

The unsaturated ester (2) (3.0 g, 17.8 mmol) was dissolved in tetrahydrofuran (20 mL) and stirred at 70° C. with nitromethane (1.92 mL, 35.6 mmol) and tetrabutylammonium fluoride (1.0 M in tetrahydrofuran, 25 mL, 25.0 mmol). After 18 hours, the mixture was cooled to room temperature, diluted with ethyl acetate (50 mL), and washed with 2N HCl (30 mL) followed by brine (50 mL). The organic phase was collected, dried (MgSO$_4$), and the solvent removed in vacuo. The residue was purified by flash chromatography (silica, ethyl acetate:heptane 1:9) to give 2.00 g (49%) of a clear oil.

$^1$H NMR 400 Mz (CDCl$_3$): δ 1.02 (3H, d, J=6 Hz), 1.08–1.37 (5H, m), 1.59–2.17 (5H, m), 2.64 (2H, m), 4.15 (2H, q, J=7 Hz), 4.64 (2H, m).

MS (ES+) m/e: 230 ([MH$^+$], 4%).

IR (film) ν cm$^{-1}$: 1183, 1377, 1548, 1732, 2956.

Synthesis of (cis/trans)-(7R)-7-Methyl-spiro[4.4]nonan-2-one (4)

The nitroester (3) (1.98 g, 8.66 mmol) was dissolved in methanol (50 mL) and shaken over Raney nickel catalyst under an atmosphere of hydrogen (40 psi) at 30° C. After 18 hours, the catalyst was removed by filtration through celite. The solvent was removed in vacuo and the residue purified by flash chromatography (silica, ethyl acetate:heptane 1:1) to give 1.05 g (79%) of a white solid.

$^1$H NMR 400 MHz (CDCl$_3$): δ 1.03 (3H, m), 1.22 (2H, m), 1.60–2.15 (5H, m), 2.22 (2H, m), 3.20 and 3.27 (2H total, 2×s, cis, and trans), 6.18 (1H, br s).

MS (ES+) m/e: 154 ([MH$^+$], 100%).

IR (film) ν cm$^{-1}$: 1695, 2949, 3231.

Synthesis of (cis/trans)-(3R)-(1-Aminomethyl-3-methyl-cyclopentyl)-acetic acid hydrochloride (5)

The lactam (4) (746 mg, 4.88 mmol) was heated to reflux in a mixture of 1,4-dioxan (5 mL) and 6N HCl (15 mL). After 4 hours, the mixture was cooled to room temperature, diluted with water (20 mL), and washed with dichloromethane (3×30 mL). The aqueous phase was collected and the solvent removed in vacuo. The residue was triturated with ethyl acetate to give a white solid which was collected and dried. This was recrystallized from ethyl acetate/methanol to give 656 mg (65%) of (5) after collection and drying.

$^1$H NMR 400 MHz (d$_6$-DMSO): δ 0.96 (3H, m), 1.01–1.24 (2H, m), 1.42–2.10 (5H, m), 2.41 and 2.44 (2H total, 2×s, cis/trans), 2.94 (2H, m), 7.96 (3H, br s), 12.35 (1H, br s).

MS (ES+) m/e: 172 ([MH-HCl]$^+$, 100%).

EXAMPLE 4

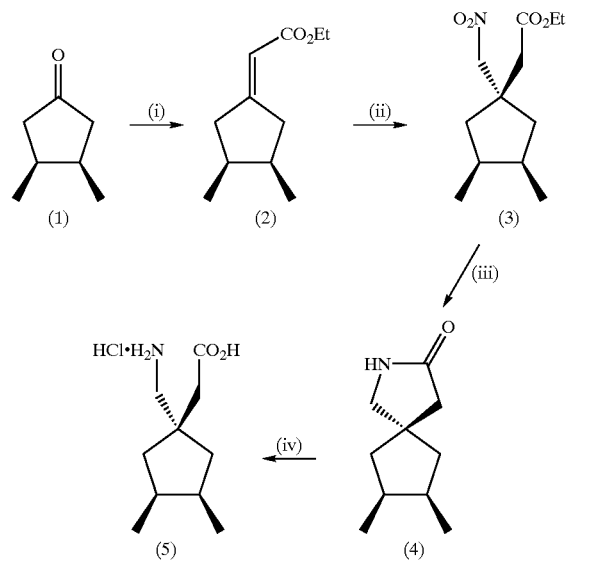

Reagents: (i) Triethylphosphonoacetate, NaH; (ii) MeNO$_2$, Bu$_4$N$^+$F$^-$; (iii) H$_2$, Ni; (iv) HCl Synthesis of (cis)-(3,4-Dimethyl-cyclopentylidene)-acetic acid ethyl ester (2)

NaH (60% dispersion in oil, 519 mg, 12.96 mmol) was suspended in dry tetrahydrofuran (30 mL) and cooled to 0° C. Triethylphosphonoacetate (2.68 mL, 13.5 mmol) was added and the mixture stirred at 0° C. for 15 minutes. The ketone (1) (1.21 g, 10.80 mmol) in THF (10 mL) was then added and the mixture allowed to warm to room temperature. After 2 hours, the mixture was partitioned between diethyl ether (200 mL) and water (150 mL). The organic phase was separated, washed with brine, dried (MgSO$_4$) and the solvent removed in vacuo. The residue was purified by flash chromatography (silica, ethyl acetate:heptane 5:95) to give 1.40 g (71%) of (2) as a colorless oil.

$^1$H NMR 400 MHz (CDCl 13): δ 0.84 (3H, d, J=6 Hz), 0.91 (3H, d, J=6 Hz), 1.26 (3H, t, J=7 Hz), 2.01–2.95 (6H, m), 4.13 (2H, q, J=7 Hz), 5.76 (1H, s).

MS (CI+) m/e: 183 ([MH$^+$], 18%).

IR (film) ν cm$^{-1}$: 1043, 1125, 1200, 1658, 1715, 2959.

Synthesis of (trans)-(3,4-Dimethyl-1-nitromethyl-cyclopentyl)-acetic acid ethyl ester (3)

The unsaturated ester (2) (1.384 g, 7.60 mmol) was dissolved in tetrahydrofuran (10 mL) and stirred at 70° C. with nitromethane (0.82 mL, 15.2 mmol) and tetrabutylammonium fluoride (1.0M in tetrahydrofuran, 11.4 mL, 11.4 mmol). After 6 hours, the mixture was cooled to room temperature, diluted with ethyl acetate (50 mL) and washed with 2N HCl (30 mL) followed by brine (50 mL). The organic phase was collected, dried (MgSO$_4$), and the solvent removed in vacuo. The residue was purified by flash chromatography (silica, ethyl acetate:heptane 5:95) to give 0.837 g (45%) of a clear oil.

$^1$H NMR 400 MHz (CDCl$_3$): δ 0.91 (6H, d, J=6 Hz), 1.21–1.39 (5H, m), 1.98 (2H, m), 2.18 (2H, m), 2.64 (2H, s), 4.15 (2H, q, J=7 Hz), 4.61 (2H, s).

MS (ES+) m/e: 244 ([MH$^+$], 8%).

IR (film) ν cm$^{-1}$: 1184, 1377, 1548, 1732, 2961.

Synthesis of (trans)-7,8-Dimethyl-spiro[4.4]nonan-2-one (4)

The nitroester (3) (0.83 g, 3.4 mmol) was dissolved in methanol (30 mL) and shaken over Raney nickel catalyst under an atmosphere of hydrogen (40 psi) at 30° C. After 4 hours, the catalyst was removed by filtration through celite. The solvent was removed in vacuo to give 567 mg (99%) of a pale yellow oil which solidified on standing.

$^1$H NMR 400 MHz (CDCl$_3$): δ 0.89 (6H, d, J=6 Hz), 1.38 (2H, m), 1.91 (2H, m), 2.10 (2H, m), 2.32 (2H, s), 3.18 (2H, s), 5.61 (1H, br s).

MS (ES+) m/e: 168 ([MH$^+$], 100%).

IR (film) ν cm$^{-1}$: 1304, 1450, 1699, 2871, 3186.

Synthesis of (1α,3β,4β)-(1-Aminomethyl-3,4-dimethyl-cyclopentyl)-acetic acid hydrochloride (5)

The lactam (4) (563 mg, 4.40 mmol) was heated to reflux in a mixture of 1,4-dioxan (5 mL) and 6N HCl (15 mL). After 4 hours, the mixture was cooled to room temperature, diluted with water (20 mL), and washed with dichloromethane (3×30 mL). The aqueous phase was collected and the solvent removed in vacuo. The residue was triturated with ethyl acetate to give a white solid which was collected and dried. This was recrystallized from ethyl acetate/methanol to give 440 mg (59%) of (5) after collection and drying.

$^1$H NMR 400 MHz (d$_6$-DMSO): δ 0.84 (6H, d, J=6 Hz), 1.21 (2H, m), 1.81 (2H, m), 2.06 (2H, m), 2.47 (2H, s), 2.89 (2H, s), 7.94 (3H, br s), 12.30 (1H, br s).

MS (ES+) m/e: 186 ([MH-HCl]$^+$, 100%).

EXAMPLE 5

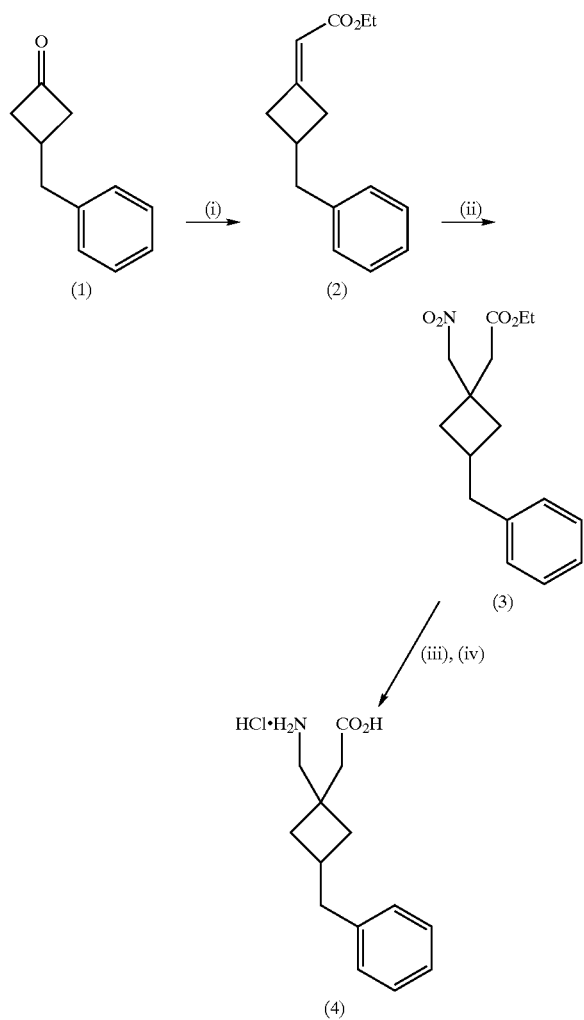

Reagents: (i) Triethylphosphonoacetate, NaH; (ii) MeNO$_2$, Bu$_4$N$^+$F$^-$; (iii) H$_2$, Ni; (iv) HCl

Synthesis of (3-Benzyl-cyclobutylidene)-acetic acid ethyl ester (2)

NaH (60% dispersion in oil, 0.496 g, 12.4 mmol), was suspended in dry tetrahydrofuran (40 mL) and cooled to 0° C. Triethylphosphonoacetate (2.58 mL, 13.0 mmol) was added and the mixture stirred at 0° C. for 15 minutes. The cyclobutanone (1) (1.89 g, 11.8 mmol) in THF (15 mL) was then added and the mixture allowed to warm to room temperature. After 4 hours, the mixture was partitoned between diethyl ether (200 mL) and water (150 mL). The organic phase was separated, washed with brine, dried (MgSO$_4$), and the solvent removed in vacuo. The residue was purified by flash chromatography (silica, ethyl acetate-:heptane 1:4) to give 2.19 g (81%) of (2) as a colorless oil.

$^1$H NMR 400 MHz (CDCl$_3$): δ 1.26 (3H, t, J=6 Hz), 2.55 (1H, m), 2.64–2.95 (5H, m), 3.28 (2H, m), 4.14 (2H, q, J=6 Hz), 5.63 (1H, s), 7.10–7.32 (5H, m).

MS (ES+) m/e: 231 ([MH$^+$], 8%).

IR (film) ν cm$^{-1}$: 1190, 1335, 1675, 1715, 2980.

Synthesis of (cis/trans)-(3-Benzyl-1-nitromethyl-cyclobutyl)-acetic acid ethyl ester (3)

The unsaturated ester (2) (2.17 g, 9.42 mmol) was dissolved in tetrahydrofuran (15 mL) and stirred at 70° C. with nitromethane (1.02 mL, 18.8 mmol) and tetrabutylammonium fluoride (1.0 M in tetrahydrofuran, 14 mL, 14.0 mmol). After 24 hours, the mixture was cooled to room temperature, diluted with ethyl acetate (150 mL), and washed with 2N HCl (60 mL) followed by brine (100 mL). The organic phase was collected, dried (MgSO$_4$) and the solvent removed in vacuo. The residue was purified by flash chromatography (silica, ethyl acetate:heptane 1:1) to give 1.55 g (57%) of a clear oil.

$^1$H NMR 400 MHz (CDCl$_3$): δ 1.25 (3H, m), 1.86 (2H, m), 2.09–2.33 (2H, m), 2.53–2.78 (3H, m), 4.15 (2H, q, J=6 Hz), 4.62 and 4.71 (2H total, 2×s, cis/trans), 7.08–7.34 (5H, m).

MS (ES+) m/e: 292 ([MH$^+$], 100%).

IR (film) ν cm$^{-1}$: 1185, 1378, 1549, 1732, 2933.

Synthesis of (cis/trans)-(1-Aminomethyl-3-benzyl-cyclobutyl)-acetic acid hydrochloride (4)

The nitroester (3) (1.53 g, 5.25 mmol) was dissolved in methanol (50 mL) and shaken over Raney nickel catalyst under an atmosphere of hydrogen (45 psi) at 30° C. After 5 hours, the catalyst was removed by filtration through celite. The solvent was removed in vacuo to give 1.32 g of a pale yellow oil which was used without purification. The oil was dissolved in 1,4-dioxane (5 mL) and 6N HCl (15 mL) and heated to reflux. After 4 hours, the mixture was cooled to room temperature, diluted with water (20 mL) and washed with dichloromethane (3×30 mL). The aqueous phase was collected and the solvent removed in vacuo. The residue was triturated with ethyl acetate to give 0.88 g (62%) of a white solid after collection and drying.

$^1$H NMR 400 MHz (d$_6$-DMSO): δ 1.64 (1H, m), 1.84 (2H, m), 2.07 (1H, m), 2.20–2.74 (5H, m), 2.98 and 3.04 (2H total, 2×s, cis/trans), 7.10–7.31 (5H, m), 8.00 (3H, br s), 12.28 (1H, br s).

MS (ES+) mr/e: 234 ([MH-HCl]$^+$, 100%).

EXAMPLE 6

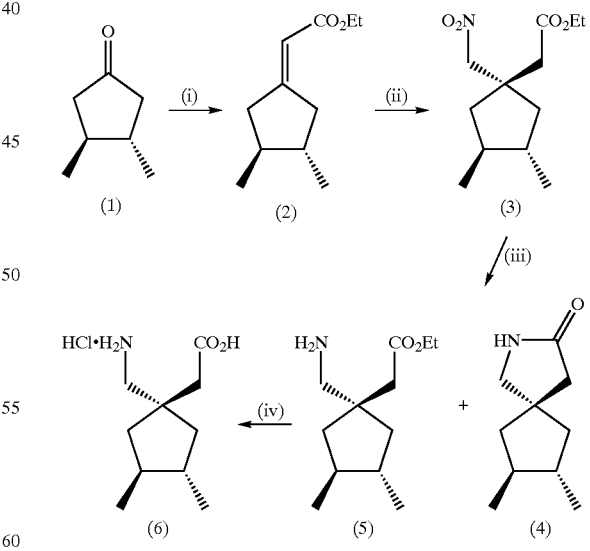

Reagents: (i) Triethylphosphonoacetate, NaH; (ii) MeNO$_2$, Bu$_4$N$^+$F$^-$; (iii) H$_2$, Ni; (iv) Hcl.

Ketone (1) is known in the literature and can be synthesized by the methods outlined therein: Y. Kato, *Chem. Pharm. Bull.*, 1966;14:1438–1439 and related references: W. C. M. C. Kokke, F. A. Varkevisser, *J. Org. Chem.*, 1974;39:1535; R. Baker, D. C. Billington, N. Eranayake, *JCS Chem. Comm.*, 1981:1234; K. Furuta, K. Iwanaga, H. Yamamoto, *Tet. Lett.,* 1986;27:4507; G. Solladie, O. Lohse, *Tet. Asymm.,* 1993;4:1547; A. Rosenquist, I. Kvarnstrom, S. C. T. Svensson, B. Classon, B. Samuelsson, *Acta Chem. Scand.,* 1992;46:1127; E. J. Corey, W. Su, *Tet. Lett.,* 1988;29:3423; D. W. Knight, B. Ojhara, *Tet. Lett.,* 1981;22:5101.

Synthesis of (trans)-(3,4-Dimethyl-cyclopentylidene)-acetic acid ethyl ester (2)

To a suspension of sodium hydride (1.3 g, 32.5 mmol) in THF (60 mL) under nitrogen at 0° C. was added triethylphosphonoacetate (6.5 mL, 32.7 mmol) over 5 minutes. After stirring for a further 10 minutes, a solution of (1) (approx. 2.68 g, approx. 30 mmol) in THF (2×10 mL) was added to the now clear solution and the ice bath removed. After 4 hours the reaction was quenched by pouring into water (100 mL) and the mixture extracted with ether (400 mL). The organic phase was washed with saturated brine (100 mL), dried and concentrated in vacuo. Column chromatography (10:1 heptane/ethyl acetate) gave the product as an oil, 4.53 g, approx. 100%; 91%.

$^1$H NMR 400 MHz (CDCl$_3$): δ 1.01 (3H, d, J=6 Hz), 1.03 (3H, d, J=6 Hz), 1.26 (3H, t, J=7 Hz), 1.49 (2H, m), 2.07 (1H, m), 2.24 (1H, m), 2.61 (1H, m), 4.13 (2H, q, J=7 Hz), 5.72 (1H, s).

MS (CI+) m/e: 183 ([MH$^+$], 21%).

Synthesis of (trans)-(3,4-Dimethyl-1-nitromethyl-cyclopentyl)-acetic acid ethyl ester (3)

To a solution of (2) (4.24 g, 23.3 mmol) in THF (15 mL) was added TBAF (32 mL of a 1 M solution in THF, 32 mmol) followed by nitromethane (3 mL) and the reaction heated at 60° C. for 8 hours. After cooling, the reaction mixture was diluted with ethyl acetate (150 mL) and washed with 2N HCl (40 mL) then saturated brine (50 mL). Column chromatography (10:1 heptane/ethyl acetate) gave the product as an oil, 2.24 g, 40%.

$^1$H NMR 400 MHz (CDCl$_3$): δ 0.98 (6H, d, J=6 Hz), 1.10–1.39 (5H, m), 1.47 (2H, m), 1.87 (1H, m), 2.03 (1H, m), 2.57 (2H, ABq, J=16, 38 Hz), 4.14 (2H, q, J=7 Hz), 4.61 (2H, ABq, J=12, 60 Hz).

MS (ES+) m/e: 244 ([MH$^+$], 5%).

IR (film) ν cm$^{-1}$: 1186, 1376, 1549, 1732, 2956.

Synthesis of (3S,4S)-(1-Aminomethyl-3,4-dimethyl-cyclopentyl)-acetic acid hydrochloride (6)

A solution of (3) (3.5 g, 14.4 mmol) in methanol (100 mL) in the presence of Ni sponge was hydrogenated at 30° C. and 50 psi for 4 hours. Filtering off the catalyst and concentrating in vacuo gave a 2:1 mixture of lactam and aminoester, 2.53 g, calculated as 96%, which was used without purification. This mixture (2.53 g, 13.8 mmol) in dioxane (15 mL) and 6N HCl (45 mL) was heated under reflux (oil bath=110° C.) for 4 hours. After cooling and diluting with water (60 mL), the mixture was washed with dichloromethane (3×50 mL) and then concentrated in vacuo. The resulting oil was washed with ethyl acetate then dichloromethane to give a sticky foam which was dried to give the product as a white powder, 2.32 g, 76%.

α$_D$ (23° C.) (H$_2$O) (c=1.002)=+28.2°.

$^1$H NMR 400 MHz (d$_6$-DMSO): δ 0.91 (6H, d, J=6 Hz), 1.18 (2H, m), 1.42 (2H, m), 1.72 (1H, m), 1.87 (1H, m), 2.42 (2H, ABq, J=16, 24 Hz), 2.90 (2H, ABq, J=12, 34 Hz), 8.00 (3H, br s), 12.34 (1H, br s).

MS (ES+) m/e: 186 ([MH-HCl]$^+$, 100%).

EXAMPLE 7

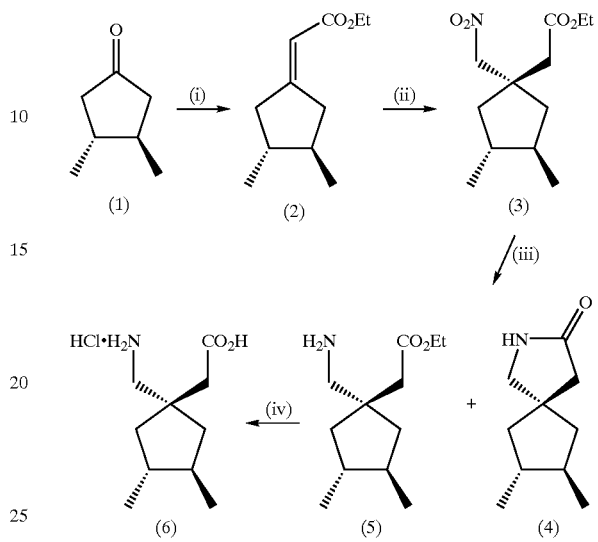

Reagents: (i) triethylphosphonoacetute, NaH; (ii) MeNO$_2$, Bu$_4$N$^+$F$^-$; (iii) H$_2$, Ni; (iv) HCl.

Ketone (1) is known in the literature and can be synthesized by the methods outlined therein: W. C. M. C. Kokke, F. A. Varkevisser, *J. Org. Chem.,* 1974;39:1535; Carnmalm, *Ark. Kemi,* 1960;15:215, 219; Carnmalm, *Chem. Ind.,* 1956:1093; Linder et al., *J. Am. Chem. Soc.,* 1977;99:727, 733; A. E. Greene, F. Charbonnier, *Tet. Lett.,* 1985;26:5525 and related references: R. Baker, D. C. Billington, N. Eranayake, *JCS Chem. Comm.,* 1981:1234; K. Furuta, K. Iwanaga, H. Yamamoto, *Tet. Lett.,* 1986;27:4507; G. Solladie, O. Lohse, *Tet. Asymm.,* 1993;4:1547; A. Rosenquist, I. Kvarnstrom, S. C. T. Svensson, B. Classon, B. Samuelsson, *Acta Chem. Scand.,* 1992;46:1127; E. J. Corey, W. Su, *Tet. Lett.,* 1988;29:3423; D. W. Knight, B. Ojhara. *Tet. Lett.,* 1981;22:5101.

Synthesis of (trans)-(3,4-Dimethyl-cyclopentylidene)-acetic acid ethyl ester (2)

To a suspension of sodium hydride (0.824 g, 20.6 mmol) in THF (40 mL) under nitrogen at 0° C. was added triethylphosphonoacetate (4.1 mL, 20.7 mmol) over 5 minutes. After stirring for a further 10 minutes, a solution of (1) (approx. 2.10 g, approx. 15.8 mmol) in THF (2×10 mL) was added to the now clear solution and the ice bath removed. After 4 hours, the reaction was quenched by pouring into water (100 mL) and the mixture extracted with ether (4×100 mL). The organic phase was washed with saturated brine (50 mL), dried and concentrated in vacuo. Column chromatography (10:1 heptane/ethyl acetate) gave the product as an oil, 2.643 g, approx. 100%; 91%.

$^1$H NMR 400 MHz (CDCl$_3$): δ 1.01 (3H, d, J=6 Hz), 1.03 (3H, d, J=6 Hz), 1.26 (3H, t, J=7 Hz), 1.49 (2H, m), 2.07 (1H, m), 2.24 (1H, m), 2.61 (1H, m), 4.13 (2H, q, J=7 Hz), 5.72 (1H, s).

MS (CI+) m/e: 183 ([MH$^+$], 19%).

Synthesis of (trans)-(3,4-Dimethyl-1-nitromethyl-cyclopentyl)-acetic acid ethyl ester (3)

To a solution of (2) (2.44 g, 13.4 mmol) in THF (12 mL) was added TBAF (18 mL of a 1 M solution in THF, 18 mmol) followed by nitromethane (2 mL) and the reaction heated at 60° C. for 4 hours. After cooling, the reaction mixture was diluted with ethyl acetate (250 mL) and washed with 2N HCl (50 mL) then saturated brine (50 mL). Column chromatography (10:1 heptane/ethyl acetate) gave the product as an oil, 1.35 1 g, 41%.

$^1$H NMR 400 MHz (CDCl$_3$): δ 0.98 (6H, d, J=6 Hz), 1.10–1.39 (5H, m), 1.47 (2H, m), 1.87 (1H, m), 2.03 (1H, m), 2.57 (2H, ABq, J=16, 38 Hz), 4.14 (2H, q, J=7 Hz), 4.61 (2H, ABq, J=12, 60 Hz).

MS (ES+) m/e: 244 ([MH$^+$], 12%).

IR (film) ν cm$^{-1}$: 1186, 1376, 1549, 1732, 2956.

Synthesis of (3R,4R)-(1-Aminomethyl-3,4-dimethyl-cyclopentyl)-acetic acid hydrochloride (6)

A solution of (3) (1.217 g, 5.0 mmol) in methanol (100 mL) in the presence of Ni sponge was hydrogenated at 30° C. and 50 psi for 4 hours. Filtering off the catalyst and concentrating in vacuo gave a 3:5 mixture of lactam and aminoester, 1.00 g, calculated as 100%, which was used without purification. This mixture (1.00 g, 5.0 mmol) in dioxane (10 mL) and 6N HCl (30 mL) was heated under reflux (oil bath=110° C.) for 4 hours. After cooling and diluting with water (100 mL), the mixture was washed with dichloromethane (2×50 mL) and then concentrated in vacuo. The resulting oil was washed with ethyl acetate then dichloromethane to give a sticky foam which was dried to give the product as a white powder, 0.532 g, 48%.

α$_D$ (23° C.) (H$_2$O) (c=1.01)=−27.0°.

$^1$H NMR 400 MHz (d$_6$-DMSO): δ 0.91 (6H, d, J=6 Hz), 1.18 (2H, m), 1.42 (2H, m), 1.72 (1H, m), 1.87 (1H, m), 2.42 (2H, ABq, J=16, 24 Hz), 2.90 (2H, ABq, J=12, 34 Hz), 8.00 (3H, br s), 12.34 (1H, br s).

MS (ES+) m/e: 186 ([MH-HCl]$^+$, 100%).

EXAMPLE 8

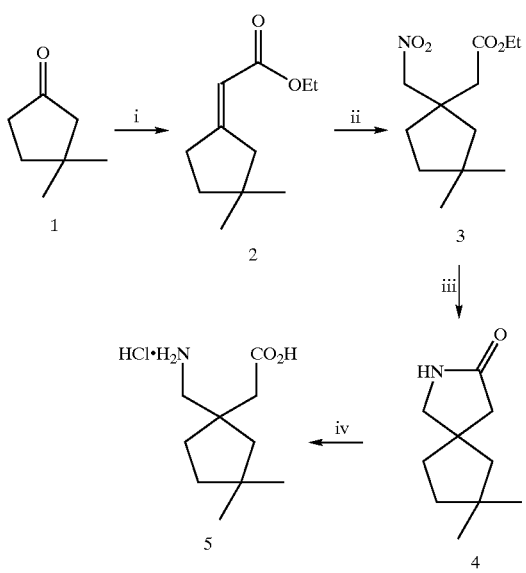

Reagents and conditions: (i) (EtO)$_2$POCH$_2$CO$_2$Et, NaH, THF; (ii) CH$_3$NO$_2$, nBu$_4$NF, THF; (iii) RaNi, H$_2$, MeOH; (iv) 6N HCl.

Synthesis of the dimethylcyclopentanone 1

3,3-Dimethylcyclopentanone was prepared according to the procedure of Hiegel and Burk, *J. Org. Chem.*, 1973;38:3637.

Synthesis of (3,3-Dimethyl-cyclopentylidene)-acetic acid ethyl ester (2)

To a stirred solution of triethylphosphonoacetate (1.84 g, 7.52 mmol) in THF (20 mL) at 0 C was added sodium hydride (300 mg of a 60% dispersion in oil). After 30 minutes, the ketone 1 (766 mg, 6.84 mmol) in THF (5 mL) was added. After 24 hours, the solution was diluted with a saturated solution of ammonium chloride and the two phases separated. The aqueous phase was extracted with diethyl ether (3×50 mL) and dried (MgSO$_4$). The combined organic phases were concentrated and flash chromatographed (25:1 hexane/ethyl acetate) to give the ester 2 as an oil, (697 mg, 56%).

$^1$H NMR (400 MHz, CDCl$_3$): δ 5.7 (1H, s), 4.1 (2H, q), 2.8 (1H, t), 2.5 (1H, t), 2.2 (1H, s), 1.55 (1H, m), 1.45 (1H, m), 1.2 (3H, t), 1.0 (3H, s), 0.98 (3H,s).

MS (m/z): 183 (MH$^+$, 100%), 224 (50%).

Synthesis of (±)-(3,3-Dimethyl-1-nitromethyl-cyclopentyl)-acetic acid ethyl ester (3)

Tetrabutylammonium fluoride (5.75 mL of a 1 M solution in THF, 5.75 mmol) was added to a solution of the ester 2 (697 mg, 3.83 mmol) and nitromethane (467 mg, 7.66 mmol) in THF (20 mL) and the mixture heated to 70° C. After 19 hours, nitromethane (233 mg, 1.9 mmol) and tetrabutylammonium fluoride (1.9 mL of a 1 M solution in TBF, 1.9 mmol) were added and reflux continued for 7 hours, whereupon the solution was cooled to room temperature, diluted with ethyl acetate (40 mL), and washed with 2N HCl (20 mL) then brine (20 mL). The organic phase was dried (MgSO$_4$) and concentrated. The crude product was flash chromatographed (9:1 hexane/ethyl acetate) to give the nitro ester 3 (380 mg, 41%) as an oil.

$^1$H NMR (400 MHz, CDCl$_3$): δ 4.62 (1H, d), 4.6 (1H, d), 4.1 (2H, q), 2.6 (1H, d), 2.58 (1H, d), 1.8 (1H, m), 1.7 (1H, m), 1.6–1.4 (4H, m), 1.2 (3H, t), 0.98 (6H, s).

MS (m/z): 244 (MH$^+$, 40%), 198 (100%).

Synthesis of (±)-7,7-Dimethyl-spiro[4.4]nonan-2-one (4)

The ester 3 (380 mg, 1.6 mmol) and Raney Nickel (1 g) were suspended in methanol (75 mL) and shaken under a hydrogen atmosphere for 24 hours. The catalyst was removed by filtration, the filtrate concentrated to give the lactam 4 (246 mg, 94%) as a white solid.

$^1$H NMR (400 MHz, CD$_3$OD): δ 3.21 (1H, d), 3.08 (1H, d), 2.24 (1H, d), 2.18 (1H, d), 1.7 (2H, m), 1.5–1.4 (4H, m), 0.98 (6H, s).

MS (m/z): 168 (MH$^+$, 40%).

Synthesis of (±)-(1-Aminomethyl-3,3-dimethyl-cyclopentyl)-acetic acid hydrochloride (5)

The lactam (240 mg, 1.44 mmol) in 6N HCl were heated to reflux for 24 hours. The residue was concentrated under reduced pressure and triturated with ether to give the amino acid 5 as a white solid.

$^1$H NMR (400 MHz, CD$_3$OD): δ 2.98 (2H, s), 2.4 (2H, s), 1.5 (2H, m), 1.4–1.2 (4H, m), 0.84 (3H, s), 0.84 (3H, s).

MS (m/z): 186 (MH$^+$, 100%), 168 (M-NH$_3$, 20%).

EXAMPLE 9

Synthesis of (cis)-(3R)-(1-Aminomethyl-3-methyl-cyclopentyl)-acetic acid hydrochloride

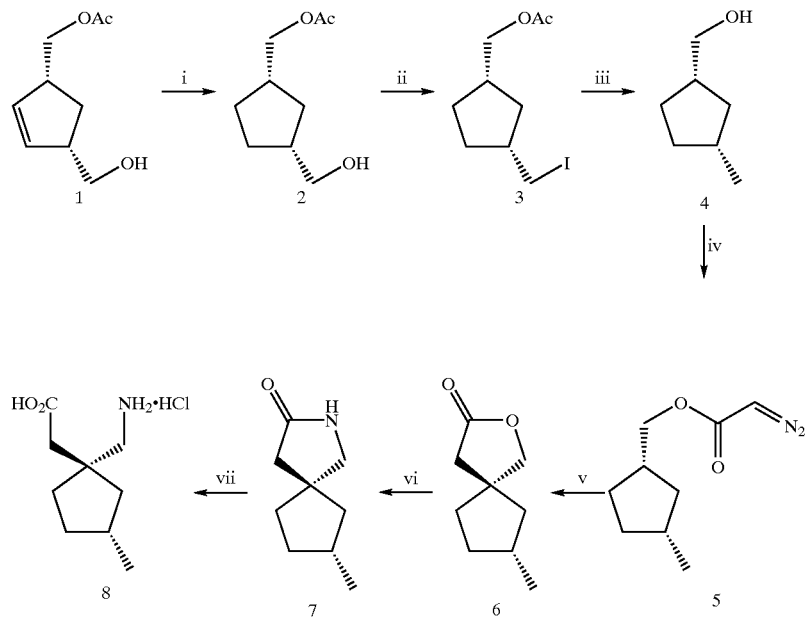

Reagents and conditions: (i) $H_2$, Pd/C, MeOH; (ii) $I_2$, $Ph_3P$, imidazole, $CH_3CN$; (iii) LAH, THF; (iv) TsNHN=CHCOCl, $PhNMe_2$, $Et_3N$; (v) $Rh_2(cap)_4$, $CH_2Cl_2$, reflux; (vi) a) $BBr_3$, EtOH; b) $NH_3$; (vii) 6N HCl, reflux.

The monoester 1 was prepared according to the procedure described in *Tetrahedron: Asymmetry* 3, 1992:431.

In the first step, the ester 1 is hydrogenated using catalysts such as Raney nickel, palladium on charcoal or rhodium catalyst or other nickel or palladium containing catalyst in a solvent such as methanol, ethanol, isopropanol, ethyl acetate, acetic acid, 1,4-dioxane, chloroform or diethyl ether at a suitable temperature in the range from 20° C. to 80° C.

In the second step, the alcohol 2 is treated with triphenylphosphine, imidazole, and iodine in a solvent such as ether, tetrahydrofuran, or acetonitrile at 0° C. to room temperature to give the iodide 3.

In the third step, the iodide 3 is treated with a suitable reducing agent such as lithium aluminium hydride or lithium borohydride in a solvent such as ether or tetrahydrofuran at temperature between 0° C. and or reflux to give the alcohol 4.

In step four, the alcohol 4 is treated with glyoxylic acid chloride (p-toluenesulfonyl)hydrazone and N,N-dimethylaniline followed by triethylamine in a solvent such as methylene chloride, chloroform, benzene, or toluene to give the diazoacetate 5.

In the fifth step, the diazoacetate 5 is added to a refluxing solution or suspension of a suitable rhodium(II) catalyst such as $Rh_2(cap)_4$, $Rh_2(5S\text{-MEOX})_4$, $Rh_2(5S\text{-MEPY})_4$, $Rh_2(5R\text{-MEPY})_4$, or $Rh_2(OAc)_4$ in a solvent such as methylene chloride, benzene, toluene, or 1,2-dichloroethane as described by Doyle and Dyatkin in *J. Org. Chem.*, 1995;60:3035 to give the spirolactone 6.

In step six, the spirolactone 6 is treated with hydrogen bromide or boron tribromide in methanol or ethanol to give a bromoester intermediate which is then reacted with ammonia to give the spirolactam 7.

In step seven, the spirolactum 7 is treated with hydrochloric acid solution (6N to 12N) at reflux to which may be added a water miscible co-solvent such as 1,4-dioxane or tetrahydrofuran to give the amino acid 8.

We claim:
1. A compound of formula

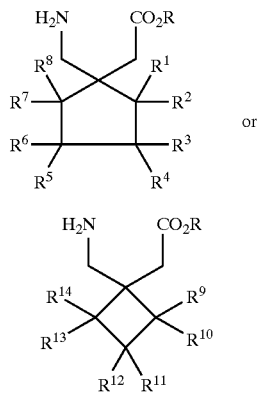

or a pharmaceutically acceptable salt thereof wherein:

R is hydrogen or a lower alkyl;

$R^1$ to $R^{14}$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, $-CO_2H$, $-CO_2R^{15}$, $-CH_2CO_2H$, $-CH_2CO_2R^{15}$, $-OR^{15}$ wherein $R^{15}$ is a straight or branched alkyl of from 1 to 6 carbons, phenyl, or benzyl, and $R^1$ to $R^8$ are not simultaneously hydrogen.

2. A compound according to claim 1 wherein $R^1$ to $R^{14}$ are selected from hydrogen, methyl, ethyl, propyl, isopropyl, butyl straight or branched, phenyl, or benzyl.

3. A compound according to claim 1 wherein $R^1$ to $R^{14}$ are selected from hydrogen, methyl, ethyl, or benzyl.

4. A compound according to claim 1 and selected from:
(1α,3α,4α)-(1-Aminomethyl-3,4-dimethyl-cyclopentyl)-acetic acid;
(1α,3α,4α)-(1-Aminomethyl-3,4-diethyl-cyclopentyl)-acetic acid;
(1α,3α,4α)-(1-Aminomethyl-3,4-diisopropyl-cyclopentyl)-acetic acid;
[1S-(1α,3α,4α)]-(1-Aminomethyl-3-ethyl-4-methyl-cyclopentyl)-acetic acid;
[1R-(1α,3α,4α)]-(1-Aminomethyl-3-ethyl-4-methyl-cyclopentyl)-acetic acid;
[1S-(1α,3α,4α)]-(1-Aminomethyl-3-isopropyl-4-methyl-cyclopentyl)-acetic acid;
[1R-(1α,3α,4α)]-(1-Aminomethyl-3-isopropyl-4-methyl-cyclopentyl)-acetic acid;
[1S-(1α,3α,4α)]-(1-Aminomethyl-3-ethyl-4-isopropyl-cyclopentyl)-acetic acid;
[1R-(1α,3α,4α)]-(1-Aminomethyl-3-ethyl-4-isopropyl-cyclopentyl)-acetic acid;
[1S-(1α,3α,4α)]-(1-Aminomethyl-3-tert-butyl-4-methyl-cyclopentyl)-acetic acid;
[1R-(1α,3α,4α)]-(1-Aminomethyl-3-tert-butyl-4-methyl-cyclopentyl)-acetic acid;
[1S-(1α,3α,4α)]-(1-Aminomethyl-3-tert-butyl-4-ethyl-cyclopentyl)-acetic acid;
[1R-(1α,3α,4α)]-(1-Aminomethyl-3-tert-butyl-4-ethyl-cyclopentyl)-acetic acid;
[1S-(1α,3α,4α)]-(1-Aminomethyl-3-tert-butyl-4-isopropyl-cyclopentyl)-acetic acid;
[1R-(1α,3α,4α)]-(1-Aminomethyl-3-tert-butyl-4-isopropyl-cyclopentyl)-acetic acid;
(1α,3α,4α)-(1-Aminomethyl-3,4-di-tert-butyl-cyclopentyl)-acetic acid;
[1S-(1α,3α,4α)]-(1-Aminomethyl-3-methyl-4-phenyl-cyclopentyl)-acetic acid;
[1R-(1α,3α,4α)]-(1-Aminomethyl-3-methyl-4-phenyl-cyclopentyl)-acetic acid;
[1S-(1α,3α,4α)]-(1-Aminomethyl-3-benzyl-4-methyl-cyclopentyl)-acetic acid;
[1R-(1α,3α,4α)]-(1-Aminomethyl-3-benzyl-4-methyl-cyclopentyl)-acetic acid;
(1S-cis)-(1-Aminomethyl-3-methyl-cyclopentyl)-acetic acid;
(1S-cis)-(1-Aminomethyl-3-ethyl-cyclopentyl)-acetic acid;
(1S-cis)-(1-Aminomethyl-3-isopropyl-cyclopentyl)-acetic acid;
(1S-cis)-(1-Aminomethyl-3-tert-butyl-cyclopentyl)-acetic acid;
(1S-cis)-(1-Aminomethyl-3-phenyl-cyclopentyl)-acetic acid;
(1S-cis)-(1-Aminomethyl-3-benzyl-cyclopentyl)-acetic acid;
(1R-cis)-(1-Aminomethyl-3-methyl-cyclopentyl)-acetic acid;
(1R-cis)-(1-Aminomethyl-3-ethyl-cyclopentyl)-acetic acid;
(1R-cis)-(1-Aminomethyl-3-isopropyl-cyclopentyl)-acetic acid;
(1R-cis)-(1-Aminomethyl-3-tert-butyl-cyclopentyl)-acetic acid;
(1R-cis)-(1-Aminomethyl-3-phenyl-cyclopentyl)-acetic acid;
(1R-cis)-(1-Aminomethyl-3-benzyl-cyclopentyl)-acetic acid;
(S)-(1-Aminomethyl-3,3-diethyl-cyclopentyl)-acetic acid;
(1-Aminomethyl-3,3,4,4-tetramethyl-cyclopentyl)-acetic acid;
(1-Aminomethyl-3,3,4,4-tetraethyl-cyclopentyl)-acetic acid;
(1α,3β,4β)-(1-Aminomethyl-3,4-dimethyl-cyclopentyl)-acetic acid;
(1α,3β,4β)-(1-Aminomethyl-3,4-diethyl-cyclopentyl)-acetic acid;
(1α,3β,4β)-(1-Aminomethyl-3,4-diisopropyl-cyclopentyl)-acetic acid;
[1R-(1α,3β,4β)]-(1-Aminomethyl-3-ethyl-4-methyl-cyclopentyl)-acetic acid;
[1S-(1α,3β,4β)]-(1-Aminomethyl-3-ethyl-4-methyl-cyclopentyl)-acetic acid;
[1R-(1α,3β,4β)]-(1-Aminomethyl-3-isopropyl-4-methyl-cyclopentyl)-acetic acid;
[1S-(1α,3β,4β)]-(1-Aminomethyl-3-isopropyl-4-methyl-cyclopentyl)-acetic acid;
[1R-(1α,3β,4β)]-(1-Aminomethyl-3-ethyl-4-isopropyl-cyclopentyl)-acetic acid;
[1S-(1α,3β,4β)]-(1-Aminomethyl-3-ethyl-4-isopropyl-cyclopentyl)-acetic acid;
[1R-(1α,3β,4β)]-(1-Aminomethyl-3-tert-butyl-4-methyl-cyclopentyl)-acetic acid;
[1S-(1α,3β,4β)]-(1-Aminomethyl-3-tert-butyl-4-methyl-cyclopentyl)-acetic acid;
[1R-(1α,3β,4β)]-(1-Aminomethyl-3-tert-butyl-4-ethyl-cyclopentyl)-acetic acid;
[1S-(1α,3β,4β)]-(1-Aminomethyl-3-tert-butyl-4-ethyl-cyclopentyl)-acetic acid;
[1R-(1α,3β,4β)]-(1-Aminomethyl-3-tert-butyl-4-isopropyl-cyclopentyl)-acetic acid;
[1S-(1α,3β,4β)]-(1-Aminomethyl-3-tert-butyl-4-isopropyl-cyclopentyl)-acetic acid;
(1α,3β,4β)-(1-Aminomethyl-3,4-di-tert-butyl-cyclopentyl)-acetic acid;
[1R-(1α,3β,4β)]-(1-Aminomethyl-3-methyl-4-phenyl-cyclopentyl)-acetic acid;
[1S-(1α,3β,4β)]-(1-Aminomethyl-3-methyl-4-phenyl-cyclopentyl)-acetic acid;
[1R-(1α,3β,4β)]-(1-Aminomethyl-3-benzyl-4-methyl-cyclopentyl)-acetic acid;
[1S-(1α,3β,4β)]-(1-Aminomethyl-3-benzyl-4-methyl-cyclopentyl)-acetic acid;
(1R-trans)-(1-Aminomethyl-3-methyl-cyclopentyl)-acetic acid;
(1R-trans)-(1-Aminomethyl-3-ethyl-cyclopentyl)-acetic acid;
(1R-trans)-(1-Aminomethyl-3-isopropyl-cyclopentyl)-acetic acid;
(1R-trans)-(1-Aminomethyl-3-tert-butyl-cyclopentyl)-acetic acid;
(1R-trans)-(1-Aminomethyl-3-phenyl-cyclopentyl)-acetic acid;
(1R-trans)-(1-Aminomethyl-3-benzyl-cyclopentyl)-acetic acid;

(1S-trans)-(1-Aminomethyl-3-methyl-cyclopentyl)-acetic acid;
(1S-trans)-(1-Aminomethyl-3-ethyl-cyclopentyl)-acetic acid;
(1S-trans)-(1-Aminomethyl-3-isopropyl-cyclopentyl)-acetic acid;
(1S-trans)-(1-Aminomethyl-3-tert-butyl-cyclopentyl)-acetic acid;
(1S-trans)-(1-Aminomethyl-3-phenyl-cyclopentyl)-acetic acid;
(1S-trans)-(1-Aminomethyl-3-benzyl-cyclopentyl)-acetic acid;
(R)-(1-Aminomethyl-3,3-diethyl-cyclopentyl)-acetic acid;
cis-(1-Aminomethyl-3-methyl-cyclobutyl)-acetic acid;
cis-(1-Aminomethyl-3-ethyl-cyclobutyl)-acetic acid;
cis-(1-Aminomethyl-3-isopropyl-cyclobutyl)-acetic acid;
cis-(1-Aminomethyl-3-tert-butyl-cyclobutyl)-acetic acid;
cis-(1-Aminomethyl-3-phenyl-cyclobutyl)-acetic acid;
trans-(1-Aminomethyl-3-methyl-cyclobutyl)-acetic acid;
trans-(1-Aminomethyl-3-ethyl-cyclobutyl)-acetic acid;
trans-(1-Aminomethyl-3-isopropyl-cyclobutyl)-acetic acid;
trans-(1-Aminomethyl-3-tert-butyl-cyclobutyl)-acetic acid;
trans-(1-Aminomethyl-3-phenyl-cyclobutyl)-acetic acid;
trans-(1-Aminomethyl-3-benzyl-cyclobutyl)-acetic acid;
cis-(1-Aminomethyl-3-ethyl-3-methyl-cyclobutyl)-acetic acid;
cis-(1-Aminomethyl-3-isopropyl-3-methyl-cyclobutyl)-acetic acid;
cis-(1-Aminomethyl-3-tert-butyl-3-methyl-cyclobutyl)-acetic acid;
cis-(1-Aminomethyl-3-methyl-3-phenyl-cyclobutyl)-acetic acid;
trans-(1-Aminomethyl-3-ethyl-3-methyl-cyclobutyl)-acetic acid;
trans-(1-Aminomethyl-3-isopropyl-3-methyl-cyclobutyl)-acetic acid;
trans-(1-Aminomethyl-3-tert-butyl-3-methyl-cyclobutyl)-acetic acid;
trans-(1-Aminomethyl-3-methyl-3-phenyl-cyclobutyl)-acetic acid;
cis-(1-Aminomethyl-3-ethyl-3-isopropyl-cyclobutyl)-acetic acid;
cis-(1-Aminomethyl-3-tert-butyl-3-ethyl-cyclobutyl)-acetic acid;
cis-(1-Aminomethyl-3-ethyl-3-phenyl-cyclobutyl)-acetic acid;
cis-(1-Aminomethyl-3-benzyl-3-ethyl-cyclobutyl)-acetic acid;
trans-(1-Aminomethyl-3-ethyl-3-isopropyl-cyclobutyl)-acetic acid;
trans-(1-Aminomethyl-3-tert-butyl-3-ethyl-cyclobutyl)-acetic acid;
trans-(1-Aminomethyl-3-ethyl-3-phenyl-cyclobutyl)-acetic acid;
trans-(1-Aminomethyl-3-benzyl-3-ethyl-cyclobutyl)-acetic acid;
cis-(1-Aminomethyl-3-tert-butyl-3-isopropyl-cyclobutyl)-acetic acid;
cis-(1-Aminomethyl-3-isopropyl-3-phenyl-cyclobutyl)-acetic acid;
trans-(1-Aminomethyl-3-benzyl-3-isopropyl-cyclobutyl)-acetic acid;
cis-(1-Aminomethyl-3-tert-butyl-3-phenyl-cyclobutyl)-acetic acid;
trans-(1-Aminomethyl-3-benzyl-3-tert-butyl-cyclobutyl)-acetic acid;
trans-(1-Aminomethyl-3-tert-butyl-3-isopropyl-cyclobutyl)-acetic acid;
trans-(1-Aminomethyl-3-isopropyl-3-phenyl-cyclobutyl)-acetic acid;
cis-(1-Aminomethyl-3-benzyl-3-isopropyl-cyclobutyl)-acetic acid;
trans-(1-Aminomethyl-3-tert-butyl-3-phenyl-cyclobutyl)-acetic acid;
cis-(1-Aminomethyl-3-benzyl-3-tert-butyl-cyclobutyl)-acetic acid;
(1-Aminomethyl-3,3-dimethyl-cyclobutyl)-acetic acid;
(1-Aminomethyl-3,3-diethyl-cyclobutyl)-acetic acid;
(1-Aminomethyl-3,3-diisopropyl-cyclobutyl)-acetic acid;
(1-Aminomethyl-3,3-di-tert-butyl-cyclobutyl)-acetic acid;
(1-Aminomethyl-3,3-diphenyl-cyclobutyl)-acetic acid;
(1-Aminomethyl-3,3-dibenzyl-cyclobutyl)-acetic acid;
(1-Aminomethyl-2,2,4,4-tetramethyl-cyclobutyl)-acetic acid;
(1-Aminomethyl-2,2,3,3,4,4-hexamethyl-cyclobutyl)-acetic acid;
(R)-(1-Aminomethyl-2,2-dimethyl-cyclobutyl)-acetic acid;
(S)-(1-Aminomethyl-2,2-dimethyl-cyclobutyl)-acetic acid;
(1R-cis)-(1-Aminomethyl-2-methyl-cyclobutyl)-acetic acid;
[1R-(1α,2α,3α)]-(1-Aminomethyl-2,3-dimethyl-cyclobutyl)-acetic acid;
(1α,2α,4α)-(1-Aminomethyl-2,4-dimethyl-cyclobutyl)-acetic acid;
[1R-(1α,2α,3β)]-(1-Aminomethyl-2,3-dimethyl-cyclobutyl)-acetic acid;
(1α,2α,4β)-(1-Aminomethyl-2,4-dimethyl-cyclobutyl)-acetic acid;
(1S-trans)-(1-Aminomethyl-2-methyl-cyclobutyl)-acetic acid;
[1S-(1α,2β,3β)]-(1-Aminomethyl-2,3-dimethyl-cyclobutyl)-acetic acid;
(1α,2β,4β)-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2β,4β)-(1-Aminomethyl-2,4-dimethyl-cyclobutyl)-acetic acid;
(1R-trans)-(1-Aminomethyl-2-methyl-cyclobutyl)-acetic acid;
[1R-(1α,2β,3β)]-(1-Aminomethyl-2,3-dimethyl-cyclobutyl)-acetic acid;
[1R-(1α,2β,4β)]-(1-Aminomethyl-2-ethyl-4-methyl-cyclobutyl)-acetic acid;
[1R-(1α,2β,3α)]-(1-Aminomethyl-2,3-dimethyl-cyclobutyl)-acetic acid;

(1α,2β,4α)-(1-Aminomethyl-2,4-dimethyl-cyclobutyl)-acetic acid;
(1S-cis)-(1-Aminomethyl-2-methyl-cyclobutyl)-acetic acid;
[1S-(1α,2α,3α)]-(1-Aminomethyl-2,3-dimethyl-cyclobutyl)-acetic acid;
[1S-(1α,2α,3α)]-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2α,4β)-(1-Aminomethyl-2,4-dimethyl-cyclobutyl)-acetic acid;
(3R, 4R)-(1-Aminomethyl-3,4-dimethyl-cyclopentyl)-acetic acid;
(3S, 4S))-(1-Aminomethyl-3,4-diethyl-cyclopentyl)-acetic acid;
(3R, 4R)-(1-Aminomethyl-3,4-diethyl-cyclopentyl)-acetic acid;
(3S, 4S)-(1-Aminomethyl-3,4-diisopropyl-cyclopentyl)-acetic acid;
(3R, 4R)-(1-Aminomethyl-3,4-diisopropyl-cyclopentyl)-acetic acid;
(3S, 4S)-(1-Aminomethyl-3,4-di-tert-butyl-cyclopentyl)-acetic acid;
(3R, 4R)-(1-Aminomethyl-3,4-di-tert-butyl-cyclopentyl)-acetic acid;
(3S, 4S)-(1-Aminomethyl-3,4-diphenyl-cyclopentyl)-acetic acid;
(3R, 4R)-(1-Aminomethyl-3,4-diphenyl-cyclopentyl)-acetic acid;
(3S, 4S)-(1-Aminomethyl-3,4-dibenzyl-cyclopentyl)-acetic acid;
(3R, 4R)-(1-Aminomethyl-3,4-dibenzyl-cyclopentyl)-acetic acid;
[1S-(1α,3α,4β)]-(1-Aminomethyl-3-methyl-4-ethyl-cyclopentyl)-acetic acid;
[1R-(1α,3β,4α)]-(1-Aminomethyl-3-methyl-4-ethyl-cyclopentyl)-acetic acid;
[1R-(1α,3α,4β)]-(1-Aminomethyl-3-methyl-4-ethyl-cyclopentyl)-acetic acid;
[1S-(1α,3β,4α)]-(1-Aminomethyl-3-methyl-4-ethyl-cyclopentyl)-acetic acid;
[1S-(1α,3α,4β)]-(1-Aminomethyl-3-methyl-4-isopropyl-cyclopentyl)-acetic acid;
[1R-(1α,3β,4α)]-(1-Aminomethyl-3-methyl-4-isopropyl-cyclopentyl)-acetic acid;
[1R-(1α,3α,4β)]-(1-Aminomethyl-3-methyl-4-isopropyl-cyclopentyl)-acetic acid;
[1S-(1α,3β,4α)]-(1-Aminomethyl-3-methyl-4-isopropyl-cyclopentyl)-acetic acid;
[1S-(1α,3α,4β)]-(1-Aminomethyl-3-methyl-4-tert-butyl-cyclopentyl)-acetic acid;
[1R-(1α,3β,4α)]-(1-Aminomethyl-3-methyl-4-tert-butyl-cyclopentyl)-acetic acid;
[1R-(1α,3α,4β)]-(1-Aminomethyl-3-methyl-4-tert-butyl-cyclopentyl)-acetic acid;
[1S-(1α,3β,4α)]-(1-Aminomethyl-3-methyl-4-tert-butyl-cyclopentyl)-acetic acid;
[1S-(1α,3α,4β)]-(1-Aminomethyl-3-methyl-4-phenyl-cyclopentyl)-acetic acid;
[1R-(1α,3β,4α)]-(1-Aminomethyl-3-methyl-4-phenyl-cyclopentyl)-acetic acid;
[1R-(1α,3α,4β)]-(1-Aminomethyl-3-methyl-4-phenyl-cyclopentyl)-acetic acid;
[1S-(1α,3β,4α)]-(1-Aminomethyl-3-methyl-4-phenyl-cyclopentyl)-acetic acid;
[1S-(1α,3α,4β)]-(1-Aminomethyl-3-benzyl-4-methyl-cyclopentyl)-acetic acid;
[1R-(1α,3β,4α)]-(1-Aminomethyl-3-benzyl-4-methyl-cyclopentyl)-acetic acid;
[1R-(1α,3α,4β)]-(1-Aminomethyl-3-benzyl-4-methyl-cyclopentyl)-acetic acid;
[1S-(1α,3β,4α)]-(1-Aminomethyl-3-benzyl-4-methyl-cyclopentyl)-acetic acid;
[1S-(1α,3α,4β)]-(1-Aminomethyl-3-ethyl-4-isopropyl-cyclopentyl)-acetic acid;
[1R-(1α,3β,4α)]-(1-Aminomethyl-3-ethyl-4-isopropyl-cyclopentyl)-acetic acid;
[1R-(1α,3α,4β)]-(1-Aminomethyl-3-ethyl-4-isopropyl-cyclopentyl)-acetic acid;
[1S-(1α,3β,4α)]-(1-Aminomethyl-3-ethyl-4-isopropyl-cyclopentyl)-acetic acid;
[1S-(1α,3α,4β)]-(1-Aminomethyl-3-tert-butyl-4-ethyl-cyclopentyl)-acetic acid;
[1R-(1α,3β,4α)]-(1-Aminomethyl-3-tert-butyl-4-ethyl-cyclopentyl)-acetic acid;
[1R-(1α,3α,4β)]-(1-Aminomethyl-3-tert-butyl-4-ethyl-cyclopentyl)-acetic acid;
[1S-(1α,3β,4α)]-(1-Aminomethyl-3-tert-butyl-4-ethyl-cyclopentyl)-acetic acid;
[1S-(1α,3α,4β)]-(1-Aminomethyl-3-ethyl-4-phenyl-cyclopentyl)-acetic acid;
[1R-(1α,3β,4α)]-(1-Aminomethyl-3-ethyl-4-phenyl-cyclopentyl)-acetic acid;
[1R-(1α,3α,4β)]-(1-Aminomethyl-3-ethyl-4-phenyl-cyclopentyl)-acetic acid;
[1S-(1α,3β,4α)]-(1-Aminomethyl-3-ethyl-4-phenyl-cyclopentyl)-acetic acid;
[1S-(1α,3α,4β)]-(1-Aminomethyl-3-benzyl-4-ethyl-cyclopentyl)-acetic acid;
[1R-(1α,3β,4α)]-(1-Aminomethyl-3-benzyl-4-ethyl-cyclopentyl)-acetic acid;
[1R-(1α,3α,4β)]-(1-Aminomethyl-3-benzyl-4-ethyl-cyclopentyl)-acetic acid;
[1S-(1α,3β,4α)]-(1-Aminomethyl-3-benzyl-4-ethyl-cyclopentyl)-acetic acid;
[1S-(1α,3α,4β)]-(1-Aminomethyl-3-tert-butyl-4-isopropyl-cyclopentyl)-acetic acid;
[1R-(1α,3β,4α)]-(1-Aminomethyl-3-tert-butyl-4-isopropyl-cyclopentyl)-acetic acid;
[1R-(1α,3α,4β)]-(1-Aminomethyl-3-tert-butyl-4-isopropyl-cyclopentyl)-acetic acid;
[1S-(1α,3β,4α)]-(1-Aminomethyl-3-tert-butyl-4-isopropyl-cyclopentyl)-acetic acid;
[1S-(1α,3α,4β)]-(1-Aminomethyl-3-isopropyl-4-phenyl-cyclopentyl)-acetic acid;
[1R-(1α,3β,4α)]-(1-Aminomethyl-3-isopropyl-4-phenyl-cyclopentyl)-acetic acid;
[1R-(1α,3α,4β)]-(1-Aminomethyl-3-isopropyl-4-phenyl-cyclopentyl)-acetic acid;
[1S-(1α,3β,4α)]-(1-Aminomethyl-3-isopropyl-4-phenyl-cyclopentyl)-acetic acid;
[1S-(1α,3α,4β)]-(1-Aminomethyl-3-benzyl-4-isopropyl-cyclopentyl)-acetic acid;

[1R-(1α,3β,4α)]-(1-Aminomethyl-3-benzyl-4-isopropyl-cyclopentyl)-acetic acid;
[1R-(1α,3α,4β)]-(1-Aminomethyl-3-benzyl-4-isopropyl-cyclopentyl)-acetic acid;
[1S-(1α,3β,4α)]-(1-Aminomethyl-3-benzyl-4-isopropyl-cyclopentyl)-acetic acid;
[1S-(1α,3α,4β)]-(1-Aminomethyl-3-tert-butyl-4-phenyl-cyclopentyl)-acetic acid;
[1R-(1α,3β,4α)]-(1-Aminomethyl-3-tert-butyl-4-phenyl-cyclopentyl)-acetic acid;
[1R-(1α,3α,4β)]-(1-Aminomethyl-3-tert-butyl-4-phenyl-cyclopentyl)-acetic acid;
[1S-(1α,3β,4α)]-(1-Aminomethyl-3-tert-butyl-4-phenyl-cyclopentyl)-acetic acid;
[1R-(1α,3α,4β)]-(1-Aminomethyl-3-benzyl-4-tert-butyl-cyclopentyl)-acetic acid;
[1S-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-tert-butyl-cyclopentyl)-acetic acid;
[1R-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-phenyl-cyclopentyl)-acetic acid;
[1R-(1α,3β,4α)]-(1-Aminomethyl-3-benzyl-4-phenyl-cyclopentyl)-acetic acid;
[1R-(1α,3α,4β)]-(1-Aminomethyl-3-benzyl-4-phenyl-cyclopentyl)-acetic acid;
[1S-(1α,3β,4α)]-(1-Aminomethyl-3-benzyl-4-phenyl-cyclopentyl)-acetic acid;
(1R-cis)-(1-Aminomethyl-2-methyl-cyclopentyl)-acetic acid;
(1S-cis)-(1-Aminomethyl-2-methyl-cyclopentyl)-acetic acid;
(1R-trans)-(1-Aminomethyl-2-methyl-cyclopentyl)-acetic acid;
(1S-trans)-(1-Aminomethyl-2-methyl-cyclopentyl)-acetic acid;
(R)-(1-Aminomethyl-2,2-dimethyl-cyclopentyl)-acetic acid;
(S)-(1-Aminomethyl-2,2-dimethyl-cyclopentyl)-acetic acid;
(1-Aminomethyl-2,2,5,5-tetramethyl-cyclopentyl)-acetic acid;
(1α,2β,5β)-(1-Aminomethyl-2,5-dimethyl-cyclopentyl)-acetic acid;
(2R, 5R)-(1-Aminomethyl-2,5-dimethyl-cyclopentyl)-acetic acid;
(2S, 5S)-(1-Aminomethyl-2,5-dimethyl-cyclopentyl)-acetic acid;
(1α,2α,5α)-(1-Aminomethyl-2,5-dimethyl-cyclopentyl)-acetic acid;
[1R-(1α,2α,3α)]-(1-Aminomethyl-2,3-dimethyl-cyclopentyl)-acetic acid;
[1R-(1α,2β,3α)]-(1-Aminomethyl-2,3-dimethyl-cyclopentyl)-acetic acid;
[1R-(1α,2α,3β)]-(1-Aminomethyl-2,3-dimethyl-cyclopentyl)-acetic acid;
[1R-(1α,2β,3β)]-(1-Aminomethyl-2,3-dimethyl-cyclopentyl)-acetic acid;
[1S-(1α,2α,3α)]-(1-Aminomethyl-2,3-dimethyl-cyclopentyl)-acetic acid;
[1S-(1α,2β,3α)]-(1-Aminomethyl-2,3-dimethyl-cyclopentyl)-acetic acid;
[1S-(1α,2α,3β)]-(1-Aminomethyl-2,3-dimethyl-cyclopentyl)-acetic acid;
[1S-(1α,2β,3β)]-(1-Aminomethyl-2,3-dimethyl-cyclopentyl)-acetic acid;
[1R-(1α,2α,4α)]-(1-Aminomethyl-2,4-dimethyl-cyclopentyl)-acetic acid;
[1S-(1α,2α,4α)]-(1-Aminomethyl-2,4-dimethyl-cyclopentyl)-acetic acid;
[1R-(1α,2α,4β)]-(1-Aminomethyl-2,4-dimethyl-cyclopentyl)-acetic acid;
[1S-(1α,2α,4β)]-(1-Aminomethyl-2,4-dimethyl-cyclopentyl)-acetic acid;
[1R-(1α,2β,4α)]-(1-Aminomethyl-2,4-dimethyl-cyclopentyl)-acetic acid;
[1S-(1α,2β,4α)]-(1-Aminomethyl-2,4-dimethyl-cyclopentyl)-acetic acid;
[1R-(1α,2β,4β)]-(1-Aminomethyl-2,4-dimethyl-cyclopentyl)-acetic acid; and
[1S-(1α,2β,4β)]-(1-Aminomethyl-2,4-dimethyl-cyclopentyl)-acetic acid.

5. A pharmaceutical composition comprising a therapeutically effective amount of a compound according to claim 1 and a pharmaceutically acceptable carrier.

* * * * *